US012735679B2

(12) United States Patent
Bao et al.

(10) Patent No.: US 12,735,679 B2
(45) Date of Patent: Sep. 15, 2026

(54) GENERATING AORTA-GONAD-MESONEPHROS-LIKE HEMATOPOIETIC CELLS FROM HUMAN PLURIPOTENT STEM CELLS UNDER A DEFINED CONDITION

(71) Applicant: Purdue Research Foundation, West Lafayette, IN (US)

(72) Inventors: Xiaoping Bao, West Lafayette, IN (US); Yun Chang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 812 days.

(21) Appl. No.: 17/800,320

(22) PCT Filed: Feb. 22, 2021

(86) PCT No.: PCT/US2021/018964
§ 371 (c)(1),
(2) Date: Aug. 17, 2022

(87) PCT Pub. No.: WO2021/173458
PCT Pub. Date: Sep. 2, 2021

(65) Prior Publication Data

US 2023/0097226 A1 Mar. 30, 2023

Related U.S. Application Data

(60) Provisional application No. 62/982,992, filed on Feb. 28, 2020.

(51) Int. Cl.
*C12N 5/0789* (2010.01)
*A61K 35/12* (2015.01)

(52) U.S. Cl.
CPC ............ *C12N 5/0647* (2013.01); *A61K 35/12* (2013.01); *C12N 2501/148* (2013.01); *C12N 2501/415* (2013.01); *C12N 2506/02* (2013.01)

(58) Field of Classification Search
None
See application file for complete search history.

(56) References Cited

U.S. PATENT DOCUMENTS

| | | | |
|---|---|---|---|
| 9,234,176 | B2 | 1/2016 | Wu et al. |
| 10,155,927 | B2 | 12/2018 | Burcin et al. |
| 2012/0021519 | A1 | 1/2012 | Ichida et al. |
| 2013/0210141 | A1 | 8/2013 | Rajesh et al. |
| 2014/0255359 | A1 | 9/2014 | Perry et al. |
| 2018/0072992 | A1* | 3/2018 | Valamehr ................ A61P 37/02 |
| 2018/0187156 | A1 | 7/2018 | Rossi et al. |
| 2018/0320137 | A1 | 11/2018 | Valamehr et al. |
| 2019/0144828 | A1 | 5/2019 | Ng et al. |
| 2020/0080059 | A1* | 3/2020 | Thomson ............. C12N 5/0636 |

FOREIGN PATENT DOCUMENTS

| | | | |
|---|---|---|---|
| CN | 108300695 | A | 7/2018 |
| WO | 2006117212 | A2 | 11/2006 |
| WO | 2009155001 | A2 | 12/2009 |
| WO | 2011115308 | A1 | 9/2011 |
| WO | 2017078807 | A1 | 5/2017 |
| WO | 2017161001 | A1 | 9/2017 |
| WO | 2019143292 | A1 | 7/2019 |

OTHER PUBLICATIONS

Choi et al., Generation of Mature Human Myelomonocytic Cells Through Expansion and Differentiation of Pluripotent Stem Cell-Derived Lin-CD34+CD43+CD45+ Progenirators, J Clinical Investigations 119: 2818-2829 (2009).
Clarke et al., The Expression of Sox17 Identifies and Regulates Haemogenic Endothelium, Nature Cell Biology 15: 502-510 (2013).
Nafria et al., Protocol for the Generation of Definitive Hematopoietic Progenitors from Human Pluripotent Stem Cells, STAR Protocols 1:100130 (2020).
Dege & Sturgeon, Directed Differentiation of Primitive and Definitive Hematopoietic Progenitors from Human Pluripotent Stem Cells, J Visualized Experiments 129: e5519 [sic, recte: e55196] (2017).
Chang et al., Chemically-defined generation of human hemogenic endothelium and definitive hematopoietic progenitor cells, Biomaterials 285(121569): 1-17 (2022).
Sturgeon et al., Wnt signaling controls the specification of definitive and primitive hematopoiesis from human pluripotent stem cells, Nature Biotechnology 32(6): 554-561 (2014), US.
Wang et al., TGF[beta] inhibition enhances the generation of hematopoietic progenitors from human ES cell-derived hemogenic endothelial cells using a stepwise strategy, Cell Research 22(1): 194-207 (2011), SG.
European Patent Office, European Search Report, EU Application No. 21761672.1, dated Mar. 27, 2024, DE.
International Search Report and Written Opinion, issued by the ISA/US, Commissioner for Patents, for International Application No. PCT/US2021/018964, mailed May 5, 2021.
Lian, X. et al., "Robust cardiomyocyte differentiation from human pluripotent stem cells via temporal modulation of canonical Wnt signaling," PNAS, 29, May 29, 2012, pp. E1848-E1857.

(Continued)

*Primary Examiner* — Blaine Lankford
(74) *Attorney, Agent, or Firm* — Reichel Stohry Dean LLP; Natalie J. Dean

(57) ABSTRACT

The present invention generally relates to a method for producing hematopoietic stem cells and progenitor cells for therapeutic uses through a two-step process manipulating the canonical Wnt signaling pathway. Started from human pluripotent stem cells, the activation of the canonical Wnt signaling pathway of those stem cells is followed by down-regulation of the Wnt signaling via various methods, including TGF-beta inhibition. Pharmaceutical composition matters and methods for treating a patient of hematopoietic diseases by administering therapeutically effective amounts of said stem cells or progenitor cells alone or together with other therapeutics are within the scope of this disclosure.

19 Claims, 18 Drawing Sheets

Specification includes a Sequence Listing.

(56) References Cited

OTHER PUBLICATIONS

Yuan, X et al., "Brief Report: Combined Chemical Treatment Enables Oct4-Induced Reprogramming from Mouse Embryonic Fibroblasts," Stem Cells, vol. 29, 2011, pp. 549-553.
Ng, E.S. et al., "Differentiation of human embryonic stem cells to HOXA+ hemogenic vasculature that resembles the aorta-gonad-mesonephros," Nature Biotechnoogy, published online Oct. 17, 2016.
Mishima, M. et al., "Two structurally distinct inhibitors of glycogen synthase kinase 3 induced centromere positive micronuclei in human lymphoblastoid TK6 cells," Mutation Research/Fundamental and Molecular Mechanisms of Mutagenesis, vol. 643, Jun. 12, 2008, pp. 29-35.
Liu et al., Chemical Modulation of Cell Fate in Stem Cell Therapeutics and Regenerative Medicine, Cell Chemical Biology 23: 893-916 (2016).
Wilkinson et al., Successful Amplification of Hematopoietic Stem Cells Using Liquid Glue, University of Tokyo [online], May 30, 2019, URL: https://www.u-tokyo.ac.jp/focus/ja/press/z0201_00077.html, [retrieved on Dec. 17, 2025].
SB 431542, Tocris Bioscience [online], Jan. 15, 2018, URL: https://web.archive.org/web/20180115032805/https://www.tocris.com/products/sb-431542_1614, [retrieved on Dec. 12, 2025].

* cited by examiner

CD45/DAPI/VE-cad/BF

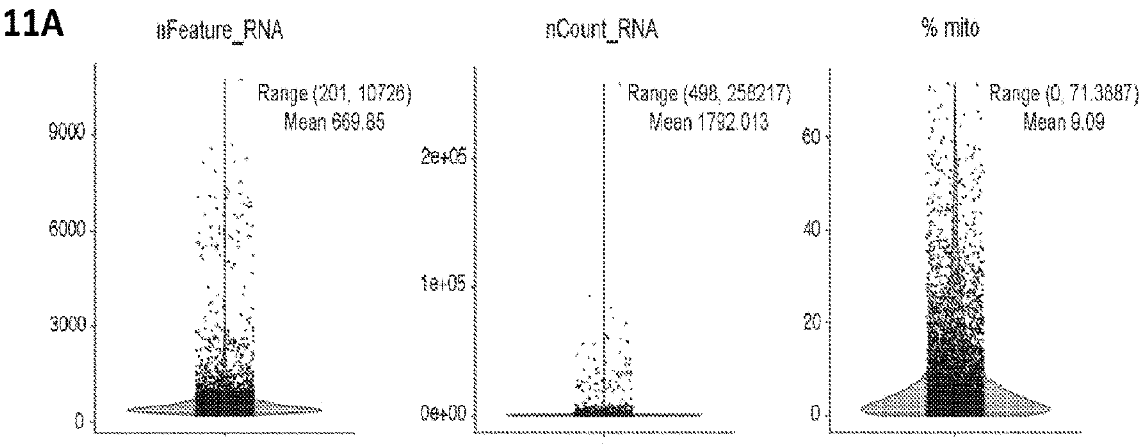
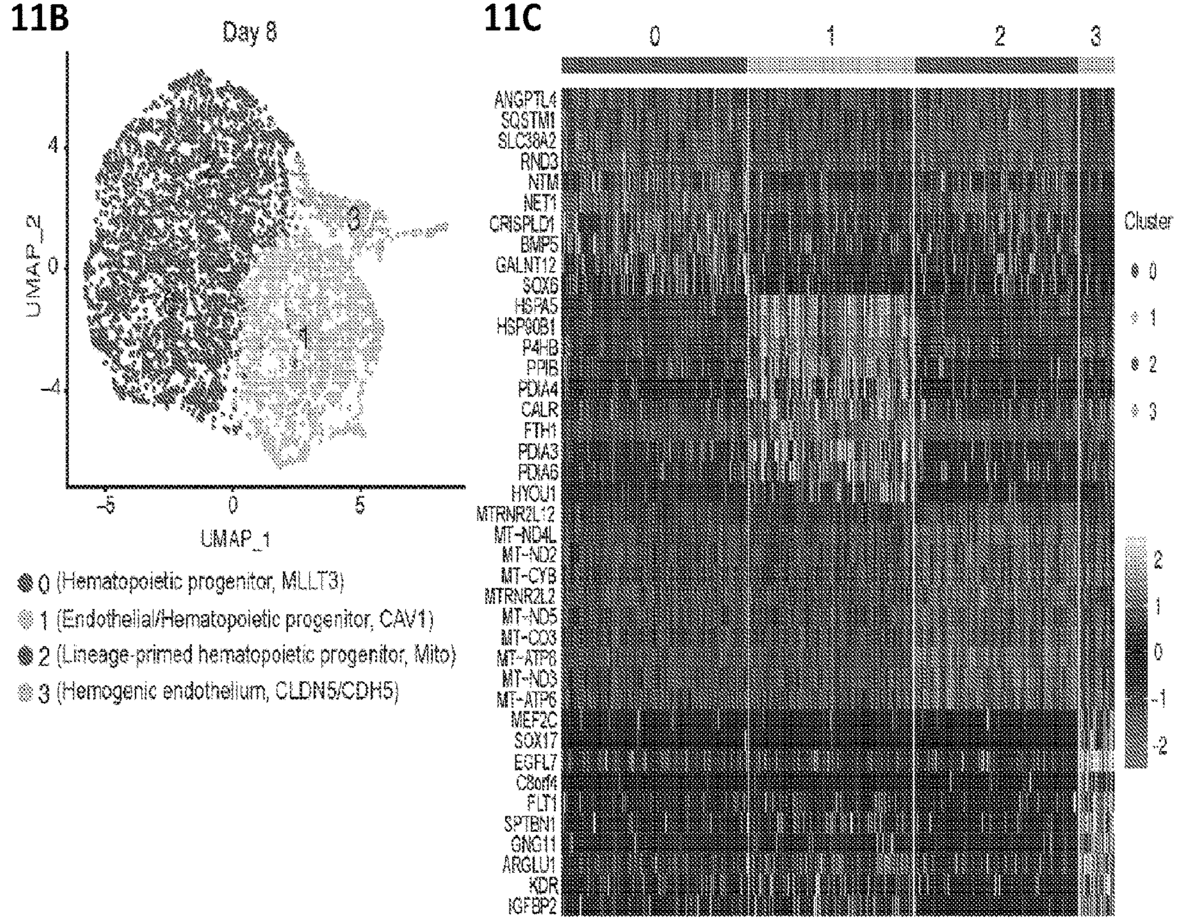
FIGS. 11A-11C

SEQUENCE LISTING

```
<160> NUMBER OF SEQ ID NOS: 16

<210> SEQ ID NO 1
<211> LENGTH: 23
<212> TYPE: DNA
<213> ORGANISM: Artificial sequence
<220> FEATURE:
<223> OTHER INFORMATION: Case9 sgRNA targeting HOXB5  seq1

<400> SEQUENCE: 1

ggctcctctg ggcgggctca ggg                                              23


<210> SEQ ID NO 2
<211> LENGTH: 23
<212> TYPE: DNA
<213> ORGANISM: Artificial sequence
<220> FEATURE:
<223> OTHER INFORMATION: Case9 sgRNA targeting HOXB5  seq2

<400> SEQUENCE: 2

atcgtaacac aaggcgaggc agg                                              23


<210> SEQ ID NO 3
<211> LENGTH: 20
<212> TYPE: DNA
<213> ORGANISM: Artificial sequence
<220> FEATURE:
<223> OTHER INFORMATION: Forward primer AXIN2

<400> SEQUENCE: 3

ctccccacct tgaatgaaga                                                  20


<210> SEQ ID NO 4
<211> LENGTH: 19
<212> TYPE: DNA
<213> ORGANISM: Artificial sequence
```

<220> FEATURE:
<223> OTHER INFORMATION: Forward primer WNT3A

<400> SEQUENCE: 4
gccccactcg gatacttct 19

<210> SEQ ID NO 5
<211> LENGTH: 23
<212> TYPE: DNA
<213> ORGANISM: Artificial sequence
<220> FEATURE:
<223> OTHER INFORMATION: Forward primer CTNNB1

<400> SEQUENCE: 5
gaatgagact gctgatcttg gac 23

<210> SEQ ID NO 6
<211> LENGTH: 20
<212> TYPE: DNA
<213> ORGANISM: Artificial sequence
<220> FEATURE:
<223> OTHER INFORMATION: Forward primer GATA2

<400> SEQUENCE: 6
gcaaccccta ctatgccaac 20

<210> SEQ ID NO 7
<211> LENGTH: 20
<212> TYPE: DNA
<213> ORGANISM: Artificial sequence
<220> FEATURE:
<223> OTHER INFORMATION: Forward primer AFP

<400> SEQUENCE: 7
aaatgcgttt ctcgttgctt 20

<210> SEQ ID NO 8
<211> LENGTH: 22
<212> TYPE: DNA
<213> ORGANISM: Artificial sequence
<220> FEATURE:
<223> OTHER INFORMATION: Forward primer ALB

<400> SEQUENCE: 8
gcacagaatc cttggtgaac ag 22

<210> SEQ ID NO 9
<211> LENGTH: 23
<212> TYPE: DNA
<213> ORGANISM: Artificial sequence
<220> FEATURE:
<223> OTHER INFORMATION: Forward primer GAPDH

<400> SEQUENCE: 9
ccccttcatt gacctcaact aca 23

<210> SEQ ID NO 10
<211> LENGTH: 21
<212> TYPE: DNA
<213> ORGANISM: Artificial sequence -continued
<220> FEATURE:
<223> OTHER INFORMATION: Forward primer HOXB5 KI (red)

<400> SEQUENCE: 10
cggctcttac ggctacaatt a 21

<210> SEQ ID NO 11
<211> LENGTH: 23
<212> TYPE: DNA
<213> ORGANISM: Artificial sequence
<220> FEATURE:
<223> OTHER INFORMATION: Forward Primer HOXB5 KI (blue)

<400> SEQUENCE: 11
ccccttcatt gacctcaact aca 23

<210> SEQ ID NO 12
<211> LENGTH: 24
<212> TYPE: DNA
<213> ORGANISM: Artificial sequence
<220> FEATURE:
<223> OTHER INFORMATION: Forward primer HOXB5 Cas9 gRNA1

<400> SEQUENCE: 12
caccggctcc tctgggcggg ctca 24

<210> SEQ ID NO 13
<211> LENGTH: 25
<212> TYPE: DNA
<213> ORGANISM: Artificial sequence
<220> FEATURE:
<223> OTHER INFORMATION: Forward primer HOXB5 Cas9 gRNA2

<400> SEQUENCE: 13
caccgatcgt aacacaaggc gaggc 25

<210> SEQ ID NO 14
<211> LENGTH: 22
<212> TYPE: DNA
<213> ORGANISM: Artificial sequence
<220> FEATURE:
<223> OTHER INFORMATION: Forward primer iscramble Cas13d gRNA

<400> SEQUENCE: 14
aaacgggtct tcgagaagac ct 22

<210> SEQ ID NO 15
<211> LENGTH: 27
<212> TYPE: DNA
<213> ORGANISM: Artificial sequence
<220> FEATURE:
<223> OTHER INFORMATION: Forward primer SOX17 Cas13d gRNA1

<400> SEQUENCE: 15
aaacaccata aattatatgc caacaca 27

<210> SEQ ID NO 16
<211> LENGTH: 27
<212> TYPE: DNA
<213> ORGANISM: Artificial sequence
<220> FEATURE:
<223> OTHER INFORMATION: Forward primer SOX17 Cas13d gRNA2

<400> SEQUENCE: 16
aaactaagat tacttgaagt aggctca 27

GENERATING AORTA-GONAD-MESONEPHROS-LIKE HEMATOPOIETIC CELLS FROM HUMAN PLURIPOTENT STEM CELLS UNDER A DEFINED CONDITION

CROSS REFERENCE TO RELATED APPLICATIONS

The present U.S. patent application is a national stage entry under 35 U.S.C. § 371(b) of International Application No. PCT/US2021/018964, filed on Feb. 22, 2021, which relates to and claims the priority benefit of U.S. Provisional Application No. 62/982,992, filed Feb. 28, 2020, the contents of which are hereby incorporated by reference in their entireties.

STATEMENT OF SEQUENCE LISTING

A computer-readable form (CRF) of the Sequence Listing is submitted with this application. The file, entitled 68927-02_Seq_Listing_ST25_txt, is generated on Feb. 15, 2021. Applicant states that the content of the computer-readable form is the same and the information recorded in computer readable form is identical to the written sequence listing

TECHNICAL FIELD

The present invention generally relates to an effective process in manufacturing stem cells for therapeutic and medical uses, in particular to a process to produce hematopoietic stem cells and progenitor cells under a defined condition from human pluripotent stem cells. Also described herein are pharmaceutical compositions and methods for treating a patient by administering therapeutically effective amounts of such stem cells so prepared alone, or together with other therapeutics, or in a pharmaceutical composition.

BACKGROUND

This section introduces aspects that may help facilitate a better understanding of the disclosure. Accordingly, these statements are to be read in this light and are not to be understood as admissions about what is or is not prior art.

Hematopoietic stem cells (HSCs) lay the foundation of hematopoiesis to generate all functional myeloid and lymphoid cells, including erythrocytes, leukocytes, platelets, immune T and natural killer (NK) cells [1,2]. Perturbations in the hematopoietic system have caused numerous diseases such as anemia, leukemia, and thrombocytopenia [1,3]. Currently, HSC transplantation and hematopoietic cell transfusion are widely used as primary treatments for these hematological diseases [2,4]. However, such therapeutic applications are limited by the lack of access to reliable cell sources of HSCs, since the number of transplantable cells conventionally from cord blood, bone marrow, and peripheral blood are insufficient, and robust cell expansion strategies are still lacking [5,6]. In addition, problems, such as shortage of human leukocyte antigen-matched donors, risk of graft-versus-host diseases, viral contamination and immunoreactions, further impede the utility of readily available HSCs [2,7]. Alternative cell sources of transplantable HSCs are thus urgently needed.

Human pluripotent stem cells (hPSCs) represent one of the potential sources for transplantable HSCs and could serve as an in vitro model for elucidating the underlying mechanisms of human hematopoiesis, due to their unique properties of unlimited self-renewal and pluripotency [2,8]. Past decade has witnessed the rapid development of methodologies for de novo hematopoietic cell generation [9], though most of them resemble yolk-sac-stage hematopoietic cells that are lack of long-term repopulating ability after transplantation [10], which is partly due to the complex nature of embryonic hematopoietic system that is composed of multiple stage-specific hematopoietic progenitor cells with distinct potential [11]. In mouse embryo, the earliest long-term repopulating HSCs arise from the aorta-gonad-mesonephros (AGM) region at embryonic day 11 [9]. The AGM also produces pre-HSCs that will home to fetal liver and mature to become repopulating HSCs [12], highlighting the importance of AGM for the definitive hematopoiesis and the need for reproducible methods to differentiate hPSCs into AGM-like HSCs. Recently, Ng et al. firstly generated AGM-like hematopoietic cells from hPSCs by stage-specific employment of cytokines and morphogens [10]. However, the resulting 3D differentiation cultures contain heterogenous SOX17+ and SOX17− vasculature as well as CD34− and CD34+ hematopoietic cells, indicating a complex environment for further investigations of molecular mechanisms. The employment of various expensive growth factors, such as Activin A, BMP4, etc, further impedes the lucrative, scalable production of hematopoietic cells to meet the clinical infusion at a nucleated cell dose of $2\times10^8$/kg [13], limiting their broader applications.

BRIEF DESCRIPTION OF THE DRAWINGS

The above and other objects, features, and advantages of the present invention will become more apparent when taken in conjunction with the following description and drawings, wherein:

FIG. 1A, A schematic of the protocol used to differentiate hPSCs towards hemogenic endothelium. FIGS. 1B-1D, 19-9-11 iPSC-derived day 5 cultures were subjected to flow cytometry analysis for CD34/CD31 (FIG. 1B) and CD34/SOX17 (FIG. 1C), and immunostaining analysis for SOX17 and VEcad (FIG. 1D). Scale bars, 100 μm. CHIR, CHIR99021; VEcad, VE-cadherin. Using an all-in-one inducible Cas13d-mediated gene knockdown system (FIG. 1E), we demonstrated that SOX17 knockdown (FIG. 1F) significantly blocked the formation of hemogenic endothelium (HE) (FIG. 1G), consistent with previous studies.

(FIG. 2A) A schematic of the protocol used to differentiate CD34+ SOX17+hPSC-derived hemogenic endothelium towards hematopoietic cells. (FIGS. 2B-2D) 19-9-11 iPSC-derived cultures differentiated as shown in (FIG. 2A) with indicated molecular signaling regulators were subjected to flow cytometry analysis for CD45 (FIG. 2B), and representative flow plots were shown in (FIG. 2C) and immunostaining images were shown in (FIG. 2D). Data are represented as mean±s.e.m of five independent replicates. (FIG. 2E) Flow cytometry analysis on CD45 of day 12 differentiated cultures with indicated Wnt and TGFβ signaling modulators were performed using H9 and 6-9-9 hPSC lines. CHIR, CHIR99021; SB, SB431542; Ctrl, control; PVA, polyvinyl alcohol; TPO, thrombopoietin; CSF, colony-stimulating factor 3.

(FIG. 3A) RT-PCR analysis of 19-9-11 iPSC-derived day 6 cells for AXIN2, WNT3A and GAPDH expression was performed and quantified. (FIGS. 3B-3C) H9 7TGP Wnt reporter hPSCs (FIG. 3B) were differentiated as illustrated in FIG. 8A with indicated signaling modulators, and day 6 differentiation cultures were subjected to flow cytometry analysis for eGFP expression (FIG. 3B). Representative flow plots were shown in (FIG. 3C). (FIGS. 3D-3G) 19-9-11 inducible shRNA CTNNB1 (beta-catenin) knockdown (ishcat) iPSCs were cultured as illustrated in FIG. 8A with or without doxycycline (dox) treatment from day 4 to day 6. At day 6, cells were subjected to RT-PCR analysis and quantified in (FIG. 3D). At day 12, cells were analyzed for CD45 expression by flow cytometry (FIG. 3E).

(FIG. 4A) A schematic of the optimized protocol for differentiation of hPSCs to hematopoietic cells. (FIGS. 4B-4F) 19-9-11 iPSCs were differentiated as illustrated in (FIG. 4A). At different time points, CD45 (FIG. 4B) and CD34/SOX17 (FIG. 4C) expression was assessed by flow cytometry. Representative flow plots of CD45 expression were shown in (FIG. 4D). RT-PCR analysis of RUNX1 and GAPDH at indicated days was performed and quantified in (FIG. 4E). Representative flow plots of CD45 expression were shown in (FIG. 4F). Scale bars, 200 μm. (FIGS. 4G-4H) 19-9-11 iPSCs were cultured as illustrated in (FIG. 4A) with or without the addition of SCF and FLT3L, and day 15 cultures were subjected for flow cytometry analysis of CD45 (FIG. 4G) and the yield of CD45+ cells were shown in (FIG. 4H).

(FIG. 5A) 3D scores plot of the first three principal components (PCs) from the principal component analysis on the RNA-sequencing data of hPSCs, hPSC-derived mesoderm (Mes), day 18 hematopoietic stem-like cells (hPSC-HSC), primary neonatal cord-blood HSCs (CB-HSC), 5-week aorta-gonad-mesonephros (AGM) endothelial, stem/progenitor and progenitor cells. Each data point corresponds to different biological samples. RNA-seq data of primary CB-HSC [35] and AGM cells [10] were obtained from previous publications. (FIG. 5B) Heatmap showing similar expression patterns of HOXA and HOXB gene clusters among hPSC-derived, CB and AGM hematopoietic cells. (FIG. 5C) UMAP embedding of day 18 scRNA-seq data colored by meta-clusters to simplify visualization. Mono: monocytes; Mye: myeloid cells; Granulo: granulocytes; Ery: erythroid cells; Mega: megakaryocytes. Violin plots of RNA counts of two hematopoietic progenitor markers PTPRC and RUNX1, and UMAP plots of two definitive and one primitive hematopoietic cell markers are shown in (FIG. 5D) and (FIG. 5E). (FIGS. 5F-5G) Violin plots of T-cell progenitor marker IL7R, and hematopoietic cell marker HOXB5 and NEO1 along different clusters are shown in (FIG. 5F) and (FIG. 5G). (FIG. 5H) VEcad-eGFP HOXB5-mCherry dual reporter H9 hPSCs were differentiated as illustrated in FIG. 4A. At different time points, HOXB5-mCherry expression was assessed by flow cytometry.

(FIGS. 6A-6B) Day 12 hPSC-derived hematopoietic cells were co-cultured with OP9-DLL4 for immune T and natural killer (NK) cell differentiation. At different time points, expression of CD4/CD8 (FIG. 6A) and CD45/CD56 (FIG. 6B) was assessed by flow cytometry. (FIGS. 6C-6D) Day 18 mCherry+CD45+hPSC-derived hematopoietic stem-like cells (HSCs) and neurons were transplanted into zebrafish and mCherry+ cells homed to caudal hematopoietic tissue (CHT) were quantified (FIG. 6C) at 5-hour post-transplantation (hpt). Representative live cell image analysis of mCherry+ cells was shown in (FIG. 6D). (FIGS. 6E-6F) Day 15 hPSC-derived mCherry+CD45+ hematopoietic cells were assessed for their homing and rescuing ability using 3-5 hpf embryos of c-myb knockout (KO) bloodless zebrafish. (FIG. 6E) Representative images of wildtype (WT) and c-myb KO bloodless zebrafish after Sudan Black Stain were shown. Scale bars, 200 μm. The survival percentage of bloodless zebrafish after cell transplantation was recorded at the indicated days post transplantation (dpt) and quantified in (FIG. 6F).

(FIG. 8A) 19-9-11 iPSCs were cultured as illustrated in FIG. 2A with SB431542 (SB) treatment at indicated days. At day 12, cells were analyzed for CD45 expression by flow cytometry. (FIGS. 8B-8C) 19-9-11 iPSCs were cultured as illustrated in (FIG. 8B) under indicated conditions. At day 12, cells were analyzed for CD45 expression by flow cytometry quantified in (FIG. 8C). CHIR, CHIR99021; SB, SB431542; HS: Human serum.

(FIGS. 9A-9D) 19-9-11 iPSCs were cultured as illustrated in FIG. 4A. Dynamic morphology changes were recorded at the indicated days (FIG. 9A) and representative 3D merged image of bright-field, CD45, VEcad and DAPI staining was shown in (FIG. 9B). (FIG. 9C) Cell viability before and after froze was assessed by flow cytometry with TO-PRO-3 Stain. (FIG. 9D) AGM-like hematopoietic cells were generated as described in FIG. 4A from 8 additional hPSC lines: H1, H9, H13, RUES2, 6-9-9, 19-9-7, Kolf2, and CT2. Scale bars, 200 m.

(FIG. 10A) Hierarchical clustering analysis of RNA-seq expression data of hPSCs, hPSC-derived mesoderm (Mes), day 18 hematopoietic stem-like cells (699- and H9-HSC), primary neonatal cord-blood HSCs (CB-HSC), 5-week aorta-gonad-mesonephros (AGM) endothelial (AGM-En), stem/progenitor (AGM-S/P), and progenitor 1 (AGM-Pr1) cells. Heat maps show hematopoietic cell-related surface markers (FIG. 10B), transcription factors (FIG. 10C) and gene ontology (GO) enrichment score over hPSCs (FIG. 10D). RNA-seq data of primary CB-HSC (4) and AGM cells (5) were obtained from previous publications.

FIGS. 11A-11D. Gene expression and trajectory analysis of day 8 endothelial and hematopoietic cells using single-cell RNA-seq (scRNA-seq). (FIG. 11A) Quality control (QC) images of Feature, RNA counts and % mitochondrial (mito) are shown. (FIG. 11B) Clustering and UMAP embedding of scRNA-seq data colored by meta-clusters to simplify visualization. (FIG. 11C) Heatmap of top 10 marker genes for each cluster is shown. (FIGS. 11D-11E) Violin plots of six genes to illustrate the transition of cells from CDH5+ CLDN5+ endothelial (FIG. 11D) to RUNX1+MLLT3+ hematopoietic progenitors (FIG. 11E). Gene expression plots of two definitive and one primitive hematopoietic cell markers are shown in (FIG. 11F). (FIG. 11G) Violin plot for GYPA, whose expression was detected only in one cell, is shown. (FIG. 11H) Pseudotime trajectory analysis using Monocle 3 of the day 8 cells identifies the developmental trajectory of hematopoietic progenitors from hemogenic endothelial cells.

(FIG. 12A) A schematic diagram of the knock-in strategy at the stop codon of the HOXB5 locus in VEcad-eGFP knock-in H9 hPSCs(6). Vertical arrows indicate the sgRNA1 and sgRNA2 targeting sites. Red and blue horizontal arrows are PCR primers for assaying HOXB5-locus targeting and homozygosity, respectively. (FIG. 12B) Representative PCR genotyping of hPSC clones after puromycin selection is shown and the expected PCR product for correctly targeted HOXB5 locus is ~16 kbp (red arrow) with an efficiency of 1 clone from a total of 17. A homozygosity assay was performed on the targeted knock-in clone 6 (C6), and it was homozygous (blue arrow). (FIGS. 12C-12D) Phase-contrast images and corresponding mCherry fluorescent images (FIG. 12C) and live-cell flow analysis of mCherry (FIG. 12D) at days 0, 5, 10, 15, and 20 after initial CHIR treatment of HOXB5-mCherry knock-in H9 were shown. BF, bright-field. Scale bars, 100 μm.

(FIGS. 13A-13C) Day 15 hPSC-derived hematopoietic cells were assessed for myeloid potential via the colony-forming unit (CFU) assay in the methylcellulose medium. After 2 weeks, the hematopoietic colonies were scored for CFUs according to cellular morphology (FIG. 13A): erythroid (CFU-E), granulocyte/macrophage (CFU-GM), macrophage (CFU-M), and multilineage progenitor (CFU-GEMM) colonies. Scale bars, 200 μm. The CFU scores were quantified in (FIG. 13B). Myeloid cells differentiated from hematopoietic cells were stained with modified Wright-Giemsa stain solution (FIG. 13C). Scale bars, 50 μm. (FIGS. 13D-13E) Day 15 hPSC-derived mCherry+CD45+ hematopoietic cells were assessed for homing ability in zebrafish. Day 15 hPSC-derived neurons were used as control (7). (FIG. 13D) A schematic diagram of the transplantation strategy for injecting hematopoietic cells in the duct of Cuvier of 48-52 hr old zebrafish. HSCs and neurons that homed to caudal hematopoietic tissue (CHT) were recorded at the indicated hours post-transplantation (hpt) (FIG. 13E). Scale bars, 100 μm. (FIGS. 13F-13G) Day 15 hPSC-derived mCherry+CD45+HSCs were assessed for their homing and rescuing ability using 48-52 hr old embryos of c-myb knockout (KO) bloodless zebrafish. Day 15 hPSC-derived neurons were used as a control (7). HSCs and neurons that homed to CHT were recorded at the indicated days post-transplantation (dpt) and quantified in (FIG. 13F). Representative fluorescent and brightfield images of the homed HSCs at 3 dpt were shown in (FIG. 13G). Scale bars, 200 μm.

DETAILED DESCRIPTION

Figures 1A, 1B, 1C, 1D, 1E, 1F, 1G:
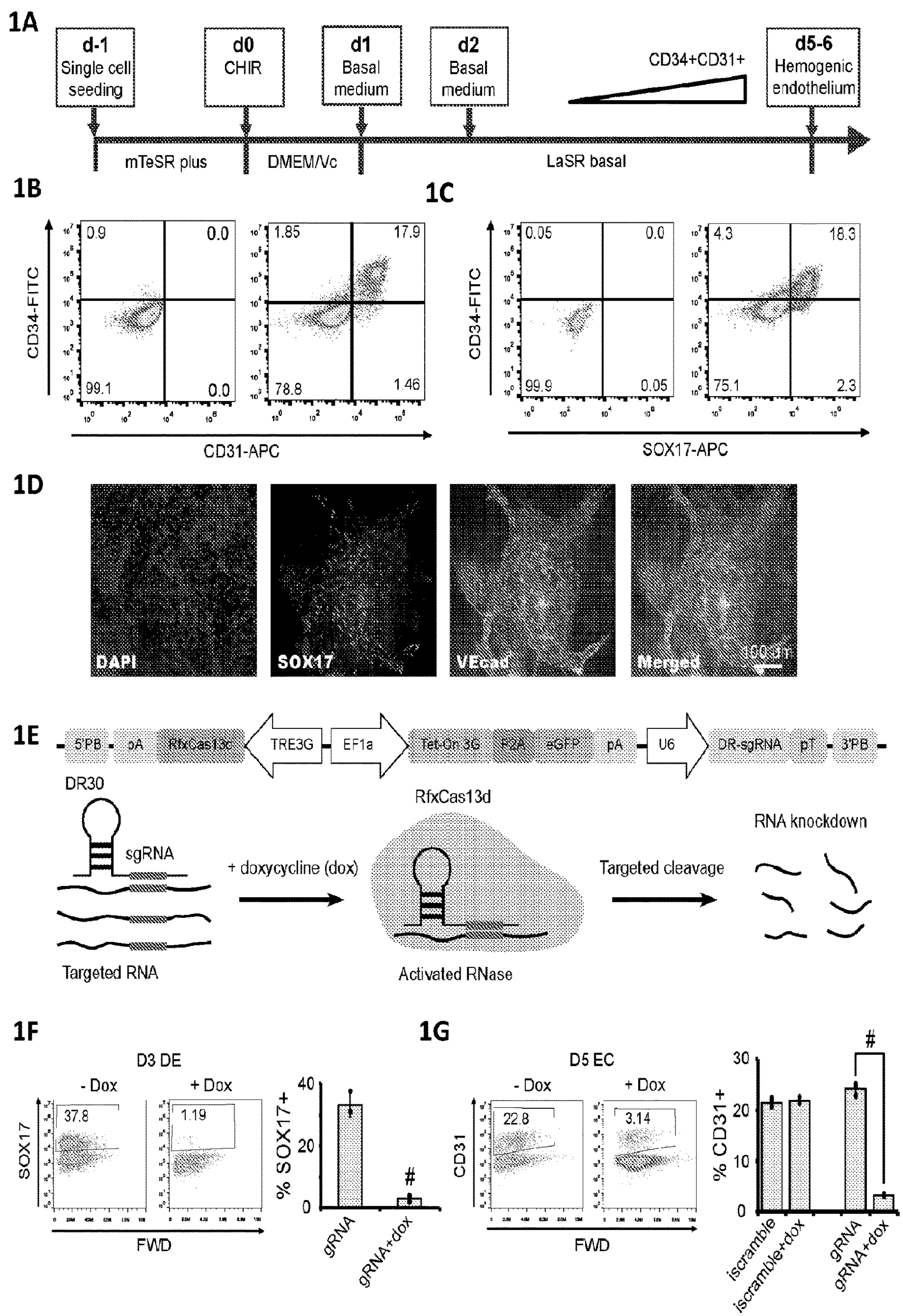
FIGS. 1A-1G. Canonical Wnt signaling specifies homogenous aorta-like CD34+SOX17+ endothelium.

For the purposes of promoting an understanding of the principles of the present disclosure, references will now be made to the embodiments illustrated in the drawings, and specific language will be used to describe the same. It will nevertheless be understood that no limitation of the scope of this disclosure is thereby intended.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, or within 99% of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators. Examples of such additives are tartrate and citrate buffers, ethanol and sequestering agents (such as ethylenediaminetetraacetic acid and its nontoxic salts). High molecular weight polymers, such as liquid polyethylene oxides, microcrystalline celluloses, carboxymethyl celluloses, polyvinylpyrrolidones, dextrans or gelatine, are suitable for regulating the viscosity. Examples of solid carrier substances are starch, lactose, mannitol, methyl cellulose, talc, highly dispersed silicic acids, high molecular weight fatty acids (such as stearic acid), gelatine, agar, calcium phosphate, magnesium stearate, animal and vegetable fats, and solid high molecular weight polymers, such as polyethylene glycol.

Preparations for parenteral administration can be present in separate dose unit forms, such as ampoules or vials. Use is preferably made of solutions of the active compound, preferably aqueous solution and, in particular, isotonic solutions and also suspensions. These injection forms can be made available as ready-to-use preparations or only be prepared directly before use, by mixing the active compound, for example the lyophilisate, where appropriate containing other solid carrier substances, with the desired solvent or suspending agent.

It is to be understood that the total daily usage of the compounds and compositions described herein may be decided by the attending physician within the scope of sound medical judgment. The specific therapeutically effective dose level for any particular patient will depend upon a variety of factors, including the disorder being treated and the severity of the disorder; activity of the specific compound employed; the specific composition employed; the age, body weight, general health, gender, and diet of the patient: the time of administration, and rate of excretion of the specific compound employed, the duration of the treatment, the drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 μg/kg to about 1 g/kg. The dosage may be single or divided, and may be administered according to a wide variety of dosing protocols, including q.d., b.i.d., t.i.d., or even every other day, once a week, once a month, and the like. In each case the therapeutically effective amount described herein corresponds to the instance of administration, or alternatively to the total daily, weekly, or monthly dose.

As used herein, the term "therapeutically effective amount" refers to that amount of active compound or pharmaceutical agent that elicits the biological or medicinal response in a tissue system, animal or human that is being sought by a researcher, veterinarian, medical doctor or other clinicians, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment.

As used herein, the term "therapeutically effective amount" refers to the amount to be administered to a patient, and may be based on body surface area, patient weight, and/or patient condition. In addition, it is appreciated that there is an interrelationship of dosages determined for humans and those dosages determined for animals, including test animals (illustratively based on milligrams per meter squared of body surface) as described by Freireich, E. J., et al., Cancer Chemother. Rep. 1966, 50 (4), 219, the disclosure of which is incorporated herein by reference. Body surface area may be approximately determined from patient height and weight (see, e.g., Scientific Tables, Geigy Pharmaceuticals, Ardley, N.Y., pages 537-538 (1970)). A therapeutically effective amount of the compounds described herein may be defined as any amount useful for inhibiting the growth of (or killing) a population of malignant cells or cancer cells, such as may be found in a patient in need of relief from such cancer or malignancy. Typically, such effective amounts range from about 5 mg/kg to about 500 mg/kg, from about 5 mg/kg to about 250 mg/kg, and/or from about 5 mg/kg to about 150 mg/kg of compound per patient body weight. It is appreciated that effective doses may also vary depending on the route of administration, optional excipient usage, and the possibility of co-usage of the compound with other conventional and non-conventional therapeutic treatments, including other anti-tumor agents, radiation therapy, and the like.

The perm "patient" as used herein includes human beings and non-human animals such as companion animals (dogs, cats and the like) and livestock animals. Livestock animals are animals raised for food production. The patient to be treated is preferably a mammal, in particular a human being.

As used herein, stem cell therapy generally refers to the use of stem cells or stem cell-derived cells to treat or prevent disease or condition. The stem cell products are also applicable to fundamental research studies. In general, any clinical application of stem cells should achieve transplantable numbers, and guaranteed high batch-to-batch consistency and reproducible efficacy, presumably low cost and high standardization. In other words, the protocols to generate stem cell products should be compatible with Good Manufacturing Practice (GMP): xeno-free, chemically defined, reproducible, cost-effective, scalable and potential to be automatic. This patent is about a chemically-defined, cost-effective, reproducible and scalable hematopoietic stem cell differentiation protocols. With further optimization and automation, the current protocol could be integrated with GMP platform to manufacture transplantable AGM-like hematopoietic stem cells for patients.

Some relevant state of the art can be found in the following publications, which are incorporated herein by reference: Haake et al. Concise Review: Towards the Clinical Translation of Induced Pluripotent Stem Cell-Derived Blood Cells-Ready for Take-off. Stem Cells Transl Med., 2019; Stem Cells and Good Manufacturing Practices: Methods, Protocols and Regulations; Shafa et al. Human Induced Pluripotent Stem Cells Manufactured Using a Current Good Manufacturing Practice-Compliant Process Differentiate Into Clinically Relevant Cells From Three Germ Layers. Front. Med., 2018; Baghbaderani, et al. cGMP-Manufactured Human Induced Pluripotent Stem Cells Are Available for Pre-clinical and Clinical Applications. Stem Cell Reports. 2015; Sousa et al. Development and Production of Good Manufacturing Practice Grade Human Embryonic Stem Cell Lines as Source Material for Clinical Application. Stem Cell Research; and Palecek S. P., et al., U.S. Pat. Nos. 9,290,741 B2, 9,765,299 B2, and 10,131,878 B2.

The Following Abbreviations are Used Herein Throughout the Specification

HSPCs: Haematopoietic stem and progenitor cells; AGM: aorta-gonad-mesonephros NK cells: natural killer cells; HSCs: hematopoietic stem cells; EHT: endothelial-to-hematopoietic transition; HE: hemogenic endothelium; hESCs: human embryonic stem cells; hPSCs: human pluripotent stem cells; BMP4: bone morphogenetic protein 4 VEGF: vascular endothelial growth factor; EPO: erythropoietin; FGF2: fibroblast growth factor 2;

CSF3: colony-stimulating factor 3; IL-6: interleukin 6; TPO: thrombopoietin PVA: polyvinyl alcohol; SCF: stem cell factor; Flt3l: FMS-like tyrosine kinase 3 ligand HEP: hemogenic endothelium progenitor; VE-cadherin: vascular endothelial cadherin OP9-DLL4: OP9-Notch ligand delta-like 4; CFU-E: cells formed erythroid; CFU-GM: granulocyte/macrophage; CFU-M: macrophage; CFU-GEMM: multilineage progenitor.

In some illustrative embodiments, the present disclosure relates to a method for generating hematopoietic stem cells and progenitor cells from human pluripotent stem cells, as well as the products and their applications.

In some illustrative embodiments, the present disclosure relates to a method for generating hematopoietic stem cells (HSCs) and progenitor cells from human pluripotent stem cells (hPSCs) comprising the step of:

a. preparing human pluripotent stem cells (hPSCs);
b. preparing a culture medium comprising a vascular endothelial growth factor (VEGF) and a glycogen synthase kinase-3 (GSK3) inhibitor, wherein said GSK3 inhibitor is to activate the canonical Wnt signaling pathway of said hPSCs;
c. culturing the hPSCs in said medium for a period of time; and
d. then downregulating the activated canonical Wnt signaling pathway or transforming growth factor beta (TGF-beta) signaling pathway for a period of time to induce and generate said hematopoietic stem cells (HSCs).

In some illustrative embodiments, the present disclosure relates to a method for generating hematopoietic stem cells (HSCs) and progenitor cells from human pluripotent stem cells (hPSCs) as disclosed herein, wherein said method further comprises addition of a stem cell factor (SCF) or a Flt3-ligand in the culture medium of step d for an improved constancy of batch to batch operation.

In some illustrative embodiments, the present disclosure relates to a method for generating hematopoietic stem cells (HSCs) and progenitor cells from human pluripotent stem cells (hPSCs) as disclosed herein, wherein said human pluripotent cells comprises human embryonic stem cell (hESC) lines selected from the group consisting of H9, H1, and H13; and human induced pluripotent cell lines selected from the group consisting of 19-9-11, 6-9-9, and Kolf2.

In some illustrative embodiments, the present disclosure relates to a method for generating hematopoietic stem cells (HSCs) and progenitor cells from human pluripotent stem cells (hPSCs) as disclosed herein, wherein said downregulating the activated canonical Wnt signaling pathway is effected by a Wnt inhibitor, heparin, SB431542, a beta-catenin shRNA, a beta-catenin-targeted Cas13d, or a Cas9 gRNA.

In some illustrative embodiments, the present disclosure relates to a method for generating hematopoietic stem cells (HSCs) and progenitor cells from human pluripotent stem cells (hPSCs) as disclosed herein, wherein said Wnt inhibitor comprises Wnt-059 and IWP2.

In some illustrative embodiments, the present disclosure relates to a method for generating hematopoietic stem cells (HSCs) and progenitor cells from human pluripotent stem cells (hPSCs) as disclosed herein, wherein said functional concentration of said Wnt inhibitor ranges from about 0.2 μM to about 20 μM.

In some illustrative embodiments, the present disclosure relates to a method for generating hematopoietic stem cells (HSCs) and progenitor cells from human pluripotent stem cells (hPSCs) as disclosed herein, wherein said Wbt-059 has a formula

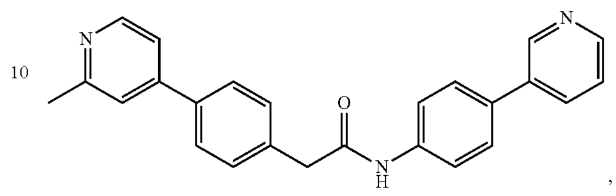

, or a pharmaceutically acceptable salt thereof.

In some illustrative embodiments, the present disclosure relates to a method for generating hematopoietic stem cells (HSCs) and progenitor cells from human pluripotent stem cells (hPSCs) as disclosed herein, wherein said IWP-2 has a formula

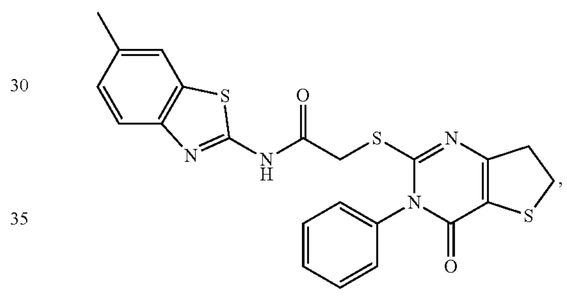

or a pharmaceutically acceptable salt thereof.

In some illustrative embodiments, the present disclosure relates to a method for generating hematopoietic stem cells (HSCs) and progenitor cells from human pluripotent stem cells (hPSCs) as disclosed herein, wherein concentration of said heparin ranges from about 0.2 to 20 μg/mL.

In some illustrative embodiments, the present disclosure relates to a method for generating hematopoietic stem cells (HSCs) and progenitor cells from human pluripotent stem cells (hPSCs) as disclosed herein, wherein said downregulating transforming growth factor beta (TGF-beta) signaling pathway is effected by a TGF-beta inhibitor, SB431542, A83-01, a ALK5 inhibitor, thrombopoietin (TPO), heparin, polyvinyl alcohol (PVA), a TGF-beta shRNA, a TGF-beta-targeted Cas13d, or a Cas9 gRNA.

In some illustrative embodiments, the present disclosure relates to a method for generating hematopoietic stem cells (HSCs) and progenitor cells from human pluripotent stem cells (hPSCs) as disclosed herein, wherein functional concentration of said SB431542 ranges from about 0.2 μM to about 20 μM.

In some illustrative embodiments, the present disclosure relates to a method for generating hematopoietic stem cells (HSCs) and progenitor cells from human pluripotent stem cells (hPSCs) as disclosed herein, wherein said SB431542 has a formula

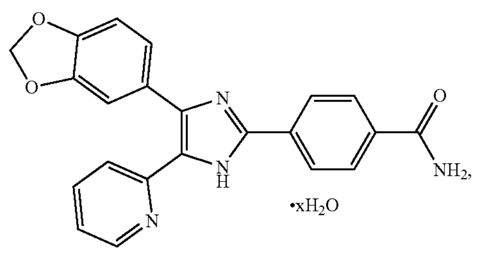 [SMILES: NC(=O)c1ccc(-c2nc(-c3ccc4c(c3)OCO4)c(-c3ccccn3)[nH]2)cc1]

or a pharmaceutically acceptable salt thereof, wherein x is any number.

In some illustrative embodiments, the present disclosure relates to a method for generating hematopoietic stem cells (HSCs) and progenitor cells from human pluripotent stem cells (hPSCs) as disclosed herein, wherein said A83-01 has a formula

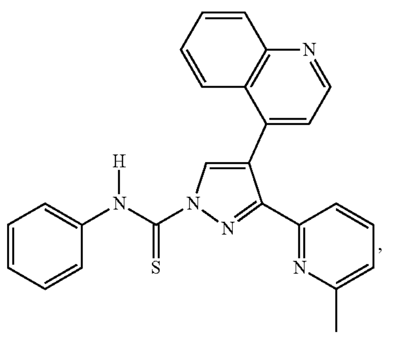 [SMILES: Cc1cccc(-c2nn(C(=S)Nc3ccccc3)cc2-c2ccnc3ccccc23)n1]

or a pharmaceutically acceptable salt thereof.

In some illustrative embodiments, the present disclosure relates to a method for generating hematopoietic stem cells (HSCs) and progenitor cells from human pluripotent stem cells (hPSCs) as disclosed herein, wherein concentration of said A83-01 ranges from about 0.2 μM to about 20 μM.

In some illustrative embodiments, the present disclosure relates to a method for generating hematopoietic stem cells (HSCs) and progenitor cells from human pluripotent stem cells (hPSCs) as disclosed herein, wherein concentration of said heparin ranges from about 0.2 μg/mL to about 20 μg/mL.

ranges from about 0.2 μM to about 20 μM.

In some illustrative embodiments, the present disclosure relates to a method for generating hematopoietic stem cells (HSCs) and progenitor cells from human pluripotent stem cells (hPSCs) as disclosed herein, wherein said GSK3 inhibitor comprises CHIR99021, CHIR98014, BIO, MeBIO, LY2090314, lithium chloride, and Indirubin.

ranges from about 0.2 μM to about 20 μM.

In some illustrative embodiments, the present disclosure relates to a method for generating hematopoietic stem cells (HSCs) and progenitor cells from human pluripotent stem cells (hPSCs) as disclosed herein, wherein said CHIR99021 has a formula

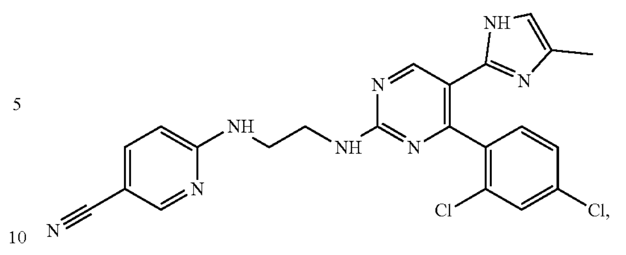

or a salt thereof.

In some illustrative embodiments, the present disclosure relates to a method for generating hematopoietic stem cells (HSCs) and progenitor cells from human pluripotent stem cells (hPSCs) as disclosed herein, wherein said CHIR98014 has a formula

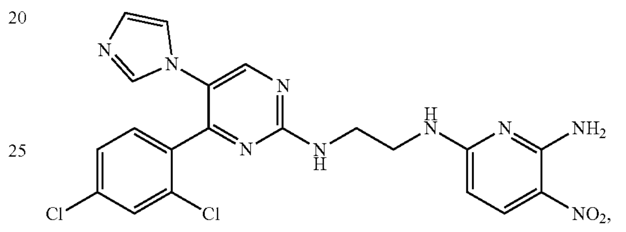

or a salt thereof.

In some illustrative embodiments, the present disclosure relates to a method for generating hematopoietic stem cells (HSCs) and progenitor cells from human pluripotent stem cells (hPSCs) as disclosed herein, wherein concentration of said heparin ranges from about 0.2 μg/mL to about 20 μg/mL.

In some illustrative embodiments, the present disclosure relates to a method for generating hematopoietic stem cells (HSCs) and progenitor cells from human pluripotent stem cells (hPSCs) as disclosed herein, wherein concentration of said CHIR99021 or CHIR98014 ranges from about 0.2 μM to about 20 μM.

In some illustrative embodiments, the present disclosure relates to a method for generating hematopoietic stem cells (HSCs) and progenitor cells from human pluripotent stem cells (hPSCs) as disclosed herein, wherein said hematopoietic stem cells are aorta-gonad-mesonephros-like $SOX17^+$ $CD34^+$ hematopoietic stem cells or progenitor cells, and general $CD34^+CD45^+/CD43^+$ hematopoietic progenitor cells.

In some other illustrative embodiments, the present disclosure relates to macrophages, neutrophils, and blood and immune cells, including NK cells, T cells, manufactured by using the resulting hematopoietic stem cells prepared according to the method as disclosed herein.

In some illustrative embodiments, the present disclosure relates to a pharmaceutical product comprising the hematopoietic stem cells manufactured according to the method of as disclosed herein.

Yet in some other illustrative embodiments, the present disclosure relates to a pharmaceutical product comprising the hematopoietic stem cells manufactured according to the method of as disclosed herein, together with one or more diluents, excipients or carriers, for use as a medicament for a patient with a hematological disease.

In some other illustrative embodiments, the present disclosure relates to a method for treating a patient of a hematological disease, comprising the step of administering a therapeutically effective amount of the product manufactured as described herein, together with one or more carriers, diluents, or excipients, to a patient in need of relief from said disease.

In some illustrative embodiments, the present disclosure relates to a kit for differentiating and manufacturing hematopoietic stem cells and progenitor cells from human pluripotent stem cells comprising a defined culture medium comprising human pluripotent stem cells, a GSK3 inhibitor, a TGF-beta inhibitor, and VEGF.

In some illustrative embodiments, the present disclosure relates to a kit for differentiating and manufacturing hematopoietic stem cells and progenitor cells from human pluripotent stem cells as disclosed herein, wherein said TGF-beta inhibitor comprises SB431542, A83-01, heparin, thrombopoietin (TPO), and polyvinyl alcohol (PVA).

In some illustrative embodiments, the present disclosure relates to a kit for differentiating and manufacturing hematopoietic stem cells and progenitor cells from human pluripotent stem cells as disclosed herein, wherein concentration of said SB431542 ranges from about 0.2 μM to about 20 μM.

In some illustrative embodiments, the present disclosure relates to a kit for differentiating and manufacturing hematopoietic stem cells and progenitor cells from human pluripotent stem cells as disclosed herein, wherein said SB431542 has a formula

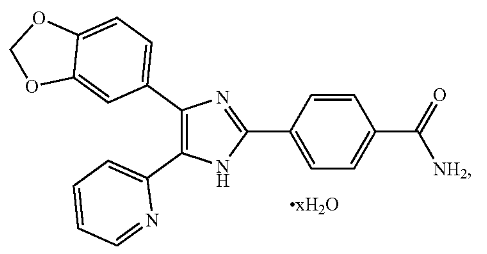 [SMILES: NC(=O)c1ccc(-c2nc(-c3ccc4c(c3)OCO4)c(-c3ccccn3)[nH]2)cc1]

or a pharmaceutically acceptable salt thereof, wherein x is a number.

In some illustrative embodiments, the present disclosure relates to a kit for differentiating and manufacturing hematopoietic stem cells and progenitor cells from human pluripotent stem cells as disclosed herein, wherein concentration of said A83-01 has a formula

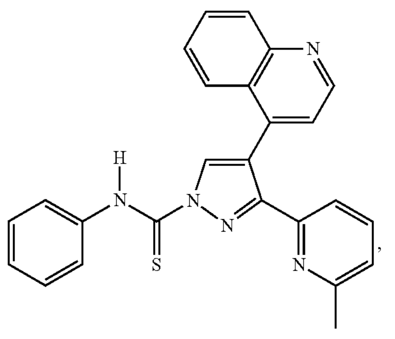 [SMILES: Cc1cccc(-c2nn(C(=S)Nc3ccccc3)cc2-c2ccnc3ccccc23)n1]

or a pharmaceutically acceptable salt thereof.

In some illustrative embodiments, the present disclosure relates to a kit for differentiating and manufacturing hematopoietic stem cells and progenitor cells from human pluripotent stem cells as disclosed herein, wherein said human pluripotent cells comprises human embryonic stem cell (hESC) lines selected from the group consisting of H9, H1, and H13; and human induced pluripotent cell lines selected from the group consisting of 19-9-11, 6-9-9, and IMR90-C4.

In some illustrative embodiments, the present disclosure relates to a kit for differentiating and manufacturing hematopoietic stem cells and progenitor cells from human pluripotent stem cells as disclosed herein, wherein said hematopoietic stem cells are aorta-gonad-mesonephros-like $SOX17^+CD34^+$ hematopoietic stem cells or progenitor cells, and general $CD34^+CD45^+/CD43^+$ hematopoietic progenitor cells.

In some illustrative embodiments, the present disclosure relates to a product of hematopoietic stem cells or progenitor cells manufactured using the kit for differentiating and manufacturing hematopoietic stem cells and progenitor cells from human pluripotent stem cells as disclosed herein.

Yet in some other illustrative embodiments, the present disclosure relates to a method for generating hematopoietic stem cells and progenitor cells from human pluripotent stem cells comprising the step of:

a. preparing human pluripotent stem cells: multiple human pluripotent cell lines were tested, including human embryonic stem cell (hESC) line H9, H1, H13, and human induced pluripotent cell line 19-9-11, 6-9-9, Kolf2;

b. hemogenic endothelial differentiation of hPSCs (day 0 to day 4 or day 5), wherein an optimal differentiation condition is as following:

Day 0, DMEM/Vc with 6 uM CHIR99021 (Gsk3 inhibitor or Wnt activator, other similar chemicals, like CHIR98014, BIO, GSK3beta inhibitor VIII, etc, or an RNAi targeted against GSK3, could also be used to replace CHIR99021). The concentration could be any other value ranging from about 0.5 to about 20 uM; DMEM/Vc could also be replaced with LaSR basal, Stemline II or other similar media;

Day 1, LaSR basal, Stemline II, StemSpan H3000, DMEM/Vc or similar medium without any other chemicals or cytokines; For more resistant H1 cell line (or some other similar non-tested cell line), 6 uM CHIR99021 (or in the concentration range) was also added to the above-mentioned medium on day 1;

Day 2-4, LaSR basal, Stemline II, StemSpan H3000, DMEM/Vc or similar medium with (for female cell lines) or without (for male cell lines, no VEGF works similarly to VEGF addition) 50 ng/mL VEGF with daily medium change (i.e., medium change on day 2 and day 3); The concentration of VEGF could range any values from about 5 to about 200 ng/mL;

c. hematopoietic specification, wherein an optimized differentiation condition is as follows:

Day 4-6, Stemline II medium with 10 uM SB431542, with or without 50 ng/mL SCF and 50 ng/mL FLT3L; the concentration of SB431542 could range from 2 uM, 4 uM, 6 uM, 8 uM, 12 uM or other values from 1 to 20 uM. In some instances, SB431542 may be replaced by 50 ng/ml thrombopoietin (TPO protein, which could range from about 1 to 200 ng/mL), or 1 ug/mL heparin (Its concentration may range from about 0.5 to 20 ug/mL), or 5 uM A83-01 (could range from 0.5 to 20 uM), among others. In order to generate comparable AGM-like hematopoietic stem cells, CSF, PVA and IL-16 could also be used, in which case a lower efficiency is normally obtained. In some other instances, 50 ng/mL of VEGF is added to the culture media to increase the overall yield of hematopoietic cells;

Day 6-20, Stemline II medium with 50 ng/mL SCF, 50 ng/mL FLT3L with medium change every 2 or 3 days;

For the hematopoietic specification stage (day 4 to day 20), Stemline II medium could be replaced with LaSR basal medium, StemSpan H3000, DMEM/Vc medium with 5 to 30% human serum, or other similar media. The concentration of SCF and FLT3L may range from 5 to 100 ng/mL. And in some instances, SCF and FLT3L are optional; and d. harvest hematopoietic stem cells;

AGM-like hematopoietic stem cells could be harvested from day 7 to day 20 (or longer) with a purity over 85% starting day 15.

In some illustrative embodiments, different differentiation factors afford a quite different yield of resulting stem cells, for example, SB431542 provides a yield of 40.9% at day 12, while most of other factors work with a lower yield, 20.6% with heparin; and 30.4% with TPO.

As disclosed herein, the method is applicable to Aorta-like hemogenic endothelium, angioblasts, endothelial cells or $Sox17^+CD31^+$cell populations (day 4 to day 8 cells), as well as general $CD34^+CD45^+/CD43^+CD44^+$definitive hematopoietic progenitor cells that are capable of NK and T cell differentiation. Additionally, the using of the resulting hematopoietic stem cells to make subsequent macrophages, neutrophils, other blood and immune cells, such as NK, T cells, is within the scope of this disclosure.

In some other illustrative embodiments, the present disclosure relates to a kit for differentiating human pluripotent stem cells into hematopoietic stem cells, not only for potential therapeutic applications, but also for fundamental studies in research labs. The methods also have valuable applications such as scalable, inexpensive, and reproducible generation of human aorta-like endothelial cells and CD34+ hematopoietic cells. The proportion of endothelial or hematopoietic cells could be further enriched using a cell separation or enrichment method, e.g., FACS, MACS, or laser-targeted ablation of non-endothelial or non-hematopoietic cells. Cells could be enriched with surface marker of CD31, CD34, CD45, CD43, CD44, e.g., by MACS, or transcription marker SOX17, RUNX1C, e.g., by FACS. After sorting, the endothelial or hematopoietic cells could be expanded over 20 fold in any of a number of known media useful for proliferation of human endothelial or hematopoietic cells, including but not limited to Human Endothelial Serum-Free medium (ThermoFisher, 11111-004), EGM-2 (Lonza, CC-3162), Endothelial Cell Culture Medium (BD Bioscience, 355054), Stemline II Hematopoietic Stem Cell Expansion Medium (Sigma, S0192), StemSpan H3000 (StemCell Technologies, 09850), and house-made human serum containing medium.

It should be pointed out that the roles of Wnt signaling activation or inhibition are stage-dependent during hematopoietic production. In order to make hematopoietic cells, initial human pluripotent stem cells need to go through mesoderm and hemogenic endothelium stages (or progenitor stages). GSK3 inhibitors, or specifically CHIR99021/CHIR98014 (etc.), is well known to efficiently convince human pluripotent stem cells to mesoderm (1 stage of hematopoietic cells), which will then become hemogenic endothelium (2nd stage) with or without VEGF (human pluripotent stem cells from female donors will need VEGF). Afterwards, Wnt inhibitor or TGF-beta inhibitor are required to efficiently promote hemogenic endothelium (2nd stage) to hematopoietic cells. And TGFbeta inhibitor may also inhibit Wnt signaling. However, it is not clearly understood for the time being that why TGFbeta inhibitor works better here to promote hematopoietic cell production.

Even though we discovered that heparin, thrombopoietin (TPO), and polyvinyl alcohol (PVA) also work well to promote hematopoietic cell production, none of them are technically a GSK3 inhibitor or a TGF-beta inhibitor.

Furthermore, a GSK3 inhibitor is also a Wnt activator. Wnt activation (by using GSK3β inhibitors, Wnt ligand proteins like Wnt3a, or optogenetics, etc.) are known to efficiently convert human pluripotent stem cells into brachyury-expressing mesoderm cells (Bao et al., 2015, 2016a, 2016b, 2017; Lian et al., 2013, 2014.2015; Qian et al., 2017; Randolph et al., 2019; Repina et al., 2019). Two commonly used GSK3β inhibitors are CHIR99021 and CHIR98014.

Self-renewing hematopoietic stem cells (HSCs) that originate from aorta-gonad-mesonephros (AGM) could regenerate the blood system after transplantation, serving as a curative therapy for numerous blood diseases. Although substantial effort has been applied to generating de novo HSC-like cells from human pluripotent stem cells (hPSCs), detailed cellular and molecular mechanisms that regulate human AGM-like hematopoiesis remain elusive. Here we demonstrated temporal manipulation of canonical Wnt signaling, in which a GSK3 inhibitor was used to activate Wnt signaling and followed by Wnt inhibition, is sufficient to induce AGM-like hematopoiesis from 11 hPSC lines. We also found Wnt inhibition is required for the hemogenic endothelium to undergo hematopoiesis, and TGFβ inhibition, through downregulation of Wnt signaling, yielded a chemically-defined, feeder-free monolayer culture platform for robust generation of homogenous AGM-like hematopoietic cells that go through the intermediate aorta-like $SOX17^+$ $CD235a^-$ hemogenic endothelium. The resulting definitive hematopoietic cells closely resembled primary cord blood HSCs at global transcript levels via RNA sequencing, and contained diverse hierarchically-primed progenitor cell populations via single cell RNA-sequencing analysis. Importantly, these definitive cells presented lymphoid and myeloid potential in vitro, and homed to the caudal hematopoietic tissue (CHT) in vivo and rescued bloodless zebrafish after transplantation. Our robust protocol for AGM-like hematopoietic cell generation holds great promise for the scalable production of multiple blood and immune cells to treat various blood diseases and cancers.

Here, we sought to build a simplified and robust differentiation platform for homogenous AGM-like hematopoietic cells by recapitulating in vivo AGM hematopoiesis. It is well-established that repopulating HSCs develop from hemogenic endothelium (HE) in arterial vasculature through the endothelial-to- hematopoietic transition (EHT) process [14-16]. Previously, we reported the robust generation of homogenous HE via GSK3 inhibition treatment in the absence of cytokines [17,18], and here we further demonstrated their AGM-like identity as marked by SOX17, a transcription factor expressed in vascular structures of AGM and required for HSC generation from AGM [10,19,20]. We also devised an all-in-one inducible Cas13d-mediated SOX17 knockdown platform and found SOX17 knockdown significantly blocked the formation of hemogenic endothelium induced by Wnt activation. TGFβ inhibition treatment significantly promoted the EHT process to generate homogenous CD45+ hematopoietic cells that co-expressed SOX17 and RUNX1, hallmarks of AGM-like hematopoietic cells [10,21]. Using an inducible shRNA CTNNB1 knockdown system, we demonstrated Wnt inhibition is sufficient to induce hematopoiesis from HE. The resulting cells closely resembled primary cord blood HSCs at global transcript levels, displayed lymphoid and myeloid potential in vitro, and homed to fish caudal hematopoietic tissue (CHT) in vivo after transplantation, mimicking aspects of human AGM hematopoiesis. Single cell RNA-sequencing (scRNA-seq) analysis identified discrete sub-populations, enriched for erythroid, myeloid, monocytic, granulocytic and megakaryocytic markers, in our hPSC-derived hematopoietic cells and trajectory analysis revealed their hierarchy. Importantly, the transplanted AGM-like hematopoietic cells also delayed the death of c-myb knockout bloodless zebrafish. Our findings provide significant advances in defining critical components for the induction of homogenous hematopoiesis in vitro, and the simplified platform will offer a robust model for human hematopoiesis studies and facilitate scalable production of hematopoietic and immune cells for potential clinical applications.

RESULTS. Canonical Wnt Signaling Specifies Homogenous Aorta-Like CD34+SOX17+Endothelium Producing hemogenic endothelium (HE) from hPSCs, marked by the expression of typical endothelial marker VE-cadherin, CD31, and CD34, is a vital step towards hematopoietic cell generation. We've previously developed a robust protocol to generate homogenous CD34+CD31+HE from hPSCs via small-molecule activation of Wnt signaling (FIG. 1A-B) [17,18]. Since simultaneous modulation of Wnt and Activin signaling yields aorta-like SOX17+ vessels in AGM that give rise to hematopoietic cells [10], we speculated that our small molecule-induced CD34+CD31+ cells are also SOX17+, which was confirmed by flow cytometry and immunostaining analysis of SOX17 expression (FIG. 1C-D). Interestingly, early CHIR99021 (CHIR) treatment in our protocol yielded a homogenous CD34+SOX17+ population, as compared to the heterogenous CD34+SOX17+ and CD34+SOX17−populations induced by Activin and later Wnt modulation [10,22], consistent with previous studies that the employment of Activin A during mesoderm induction favors primitive hematopoiesis [8,23]. Importantly, the resulting CD34+SOX17+AGM-like HE didn't express CD235a, markers of primitive hematopoiesis [24]. Using an all-in-one inducible Cas13d-mediated gene knockdown system (FIG. 1E), we demonstrated that SOX17 knockdown (FIG. 1F) significantly blocked the formation of hemogenic endothelium (HE) (FIG. 1G), consistent with previous studies [25,26].

Screening Developmental Signaling Pathways Reveals Contribution from Wnt and TGFβ Inhibitions to the Hematopoiesis of Hemogenic Endothelium.

Figures 2A, 2B, 2C, 2D, 2E:
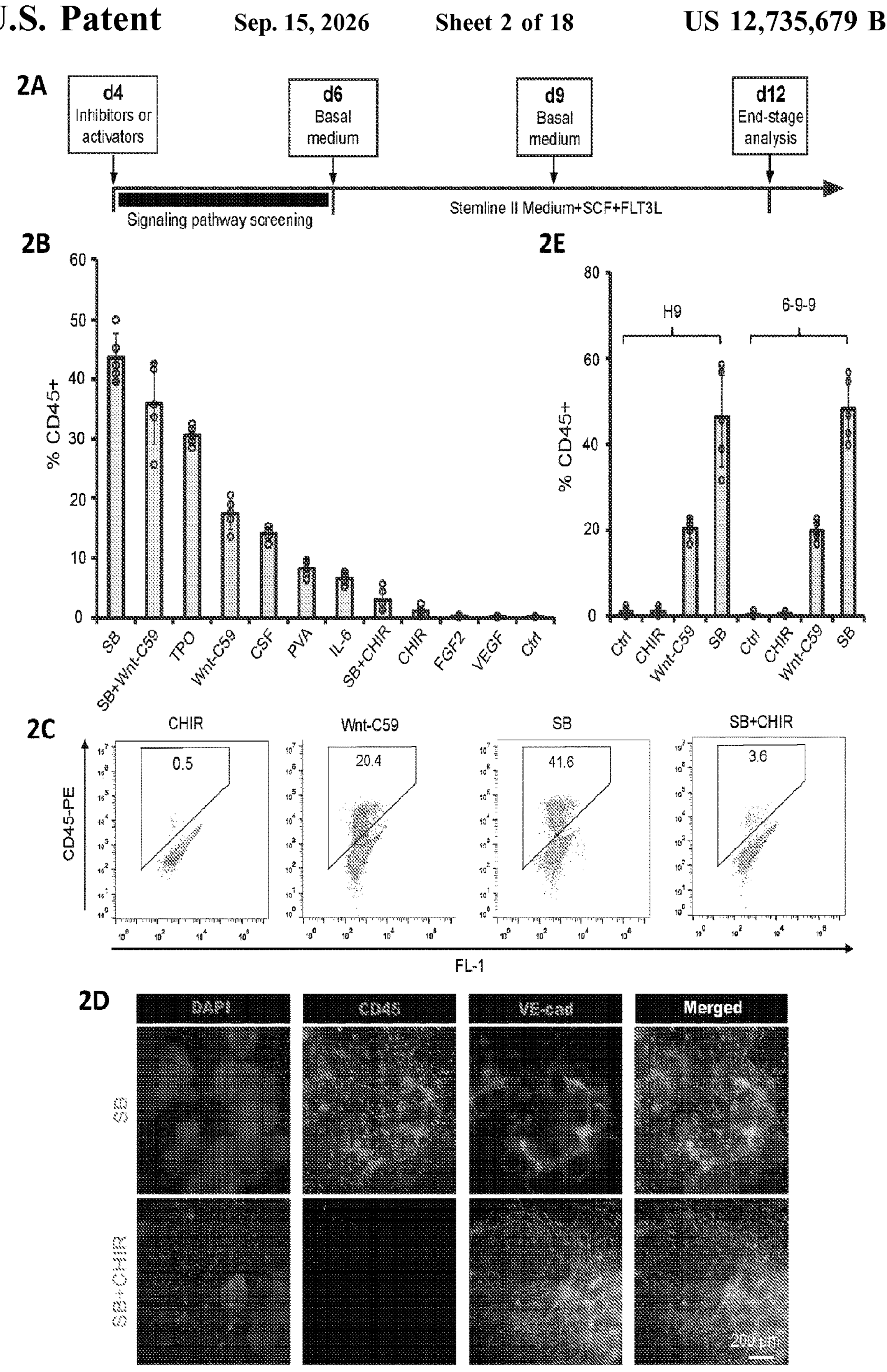
FIGS. 2A-2E. Wnt and TGFβ inhibitors significantly induce hematopoiesis of hemogenic endothelium.

Many signaling pathways, including Wnt [10,24], TGFβ [27], BMP [28,29], retinoic acid [30], Notch [31], etc., and their cross-talks have been shown to regulate hematopoietic cell specification at multiple stages, which may play important roles during in vitro hematopoiesis. While OP9-DLL4 stromal cells have been used to efficiently induce hematopoietic and immune cells from our small-molecule induced HE [32], the undefined nature of feeder cells may lead to inaccurate investigation of signaling pathways during hematopoiesis. Thus, to develop a chemically-defined hematopoietic specification platform, screening of known chemicals and cytokines was performed on our hPSC-derived AGM-like HE under feeder-free conditions (FIG. 2A). SB431542 (SB) treatment outperformed all of other screened modulators and significantly enhanced the generation of CD45+ hematopoietic cells (FIG. 2B-D). Interestingly, Wnt-059, a Wnt inhibitor, also significantly induced the emergence of hematopoietic cells, while activation of Wnt signaling by CHIR blocked the hematopoiesis induced by SB. Wnt-059 and SB-induced hematopoiesis were also applicable to H9 and 6-9-9 hPSCs (FIG. 2E). Notably, a higher hematopoietic specifying efficiency was observed under SB treatment, suggesting a potential cross-talk between TGFβ and other signaling pathways, such as retinoic acid signaling [30], in addition to the Wnt inhibition, for the SB-induced hematopoiesis. Collectively, our results demonstrate that TGFβ and Wnt inhibition significantly enhances the hematopoiesis of hPSC-derived HE, offering an accessible simple platform for further detailed investigation of the signaling pathways involved in human hematopoiesis.

Figures 3A, 3B, 3C, 3D, 3E:
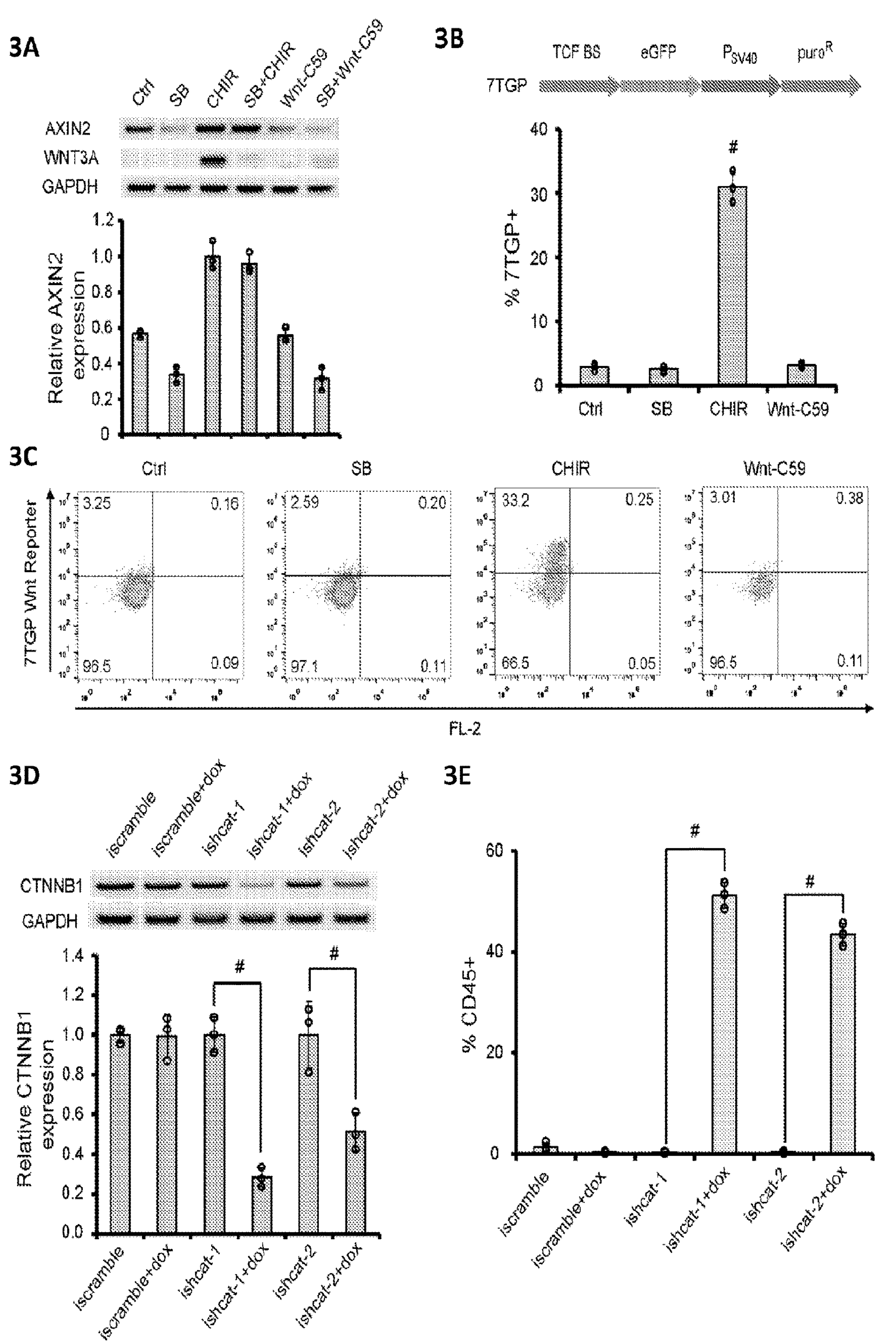
FIGS. 3A-3E. Wnt inhibition is sufficient for the AGM-like hematopoiesis.

Wnt Inhibition is Sufficient to Induce Hematopoiesis of AGM-Like Hemogenic Endothelium To further investigate the role of Wnt signaling during hematopoiesis, we performed RT-PCR analysis on the day 6 HE samples under different conditions, and low expression of WNT3A and AXIN2 (FIG. 3A), a downstream target of Wnt signaling, as well as low transcriptional activity of endogenous Wnt signaling in a 7TGP Wnt reporter line (FIG. 3B-C), were observed in both SB and Wnt-059 cultures, indicating an important role of Wnt inhibition at this stage. CTNNB1 knockdown via inducible beta-catenin shRNA (ishcat) [33] further confirmed the sufficiency of Wnt inhibition for the hematopoiesis of HE (FIG. 3D-E). These findings were consistent with previous reports that genes antagonizing canonical Wnt signaling are enriched in human AGM cells [10], and Wnt inhibition is required for hematopoietic transition from mouse AGM [30].

Figures 4A, 4B, 4C, 4D, 4E, 4F, 4G, 4H:
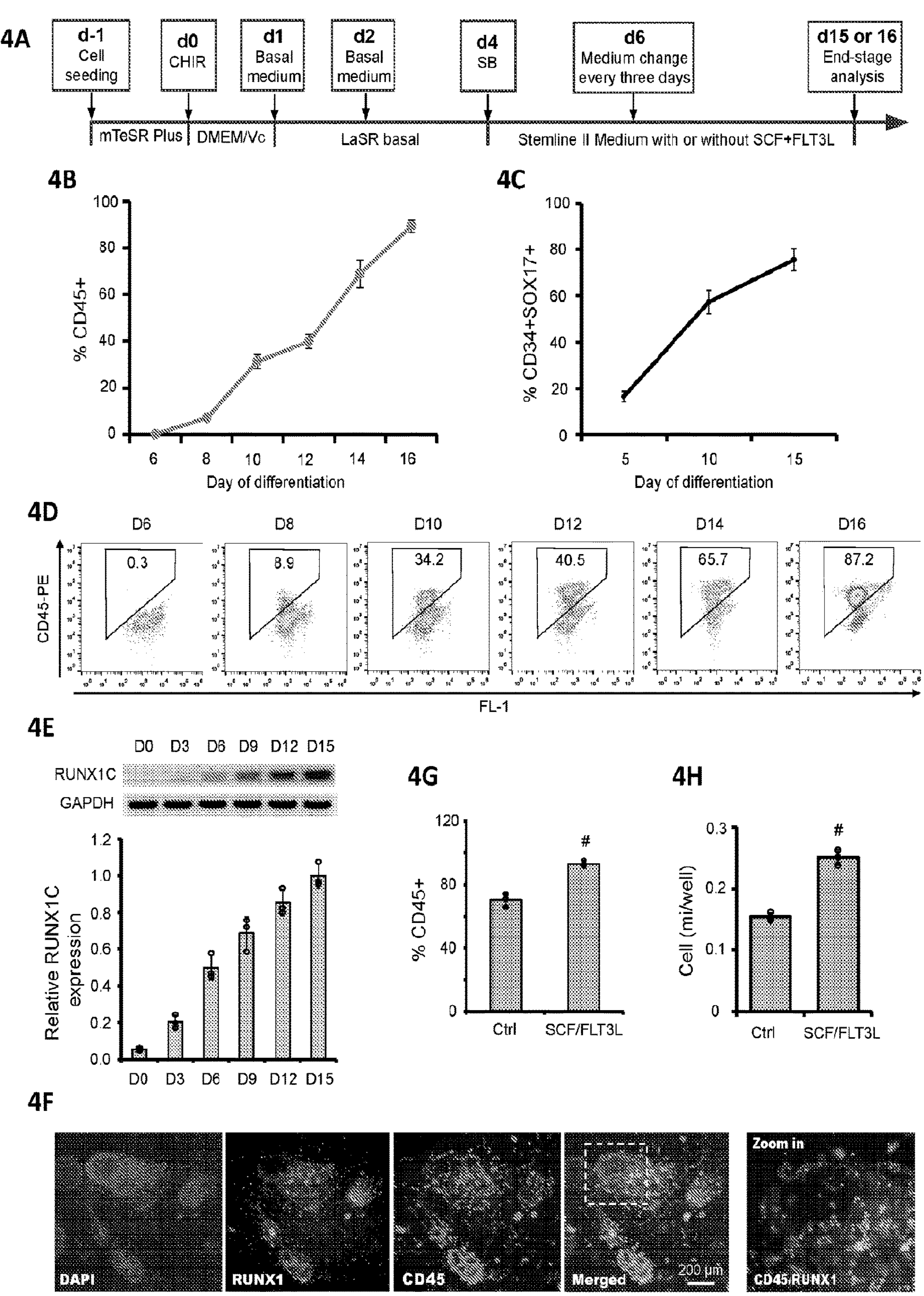
FIGS. 4A-4H. Chemically-defined conditions for robust AGM-like hematopoietic cell generation.
Figure 8A:
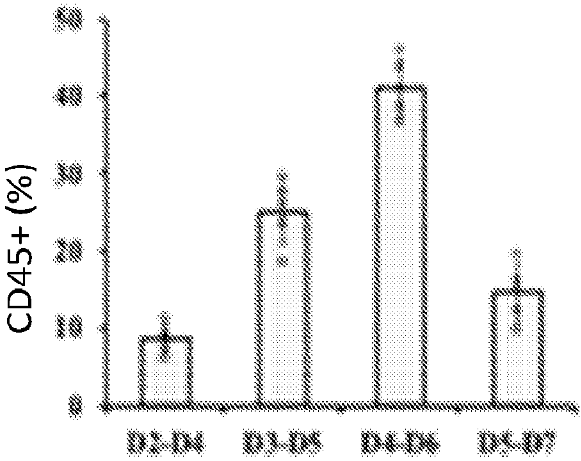
FIGS. 8A-8C. Chemically-defined, xeno-free, and serum-free conditions to generate CD45+ hematopoietic cells.
Figure 8B:
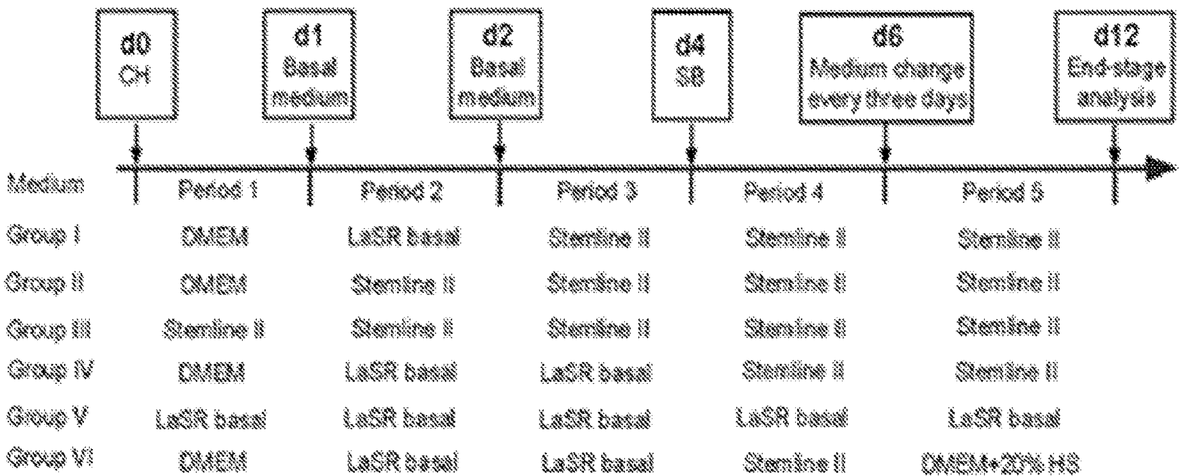
Figure 8C:
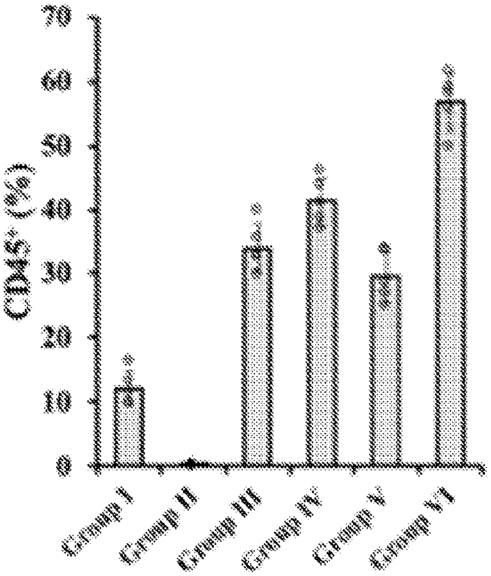
Figure 9A:
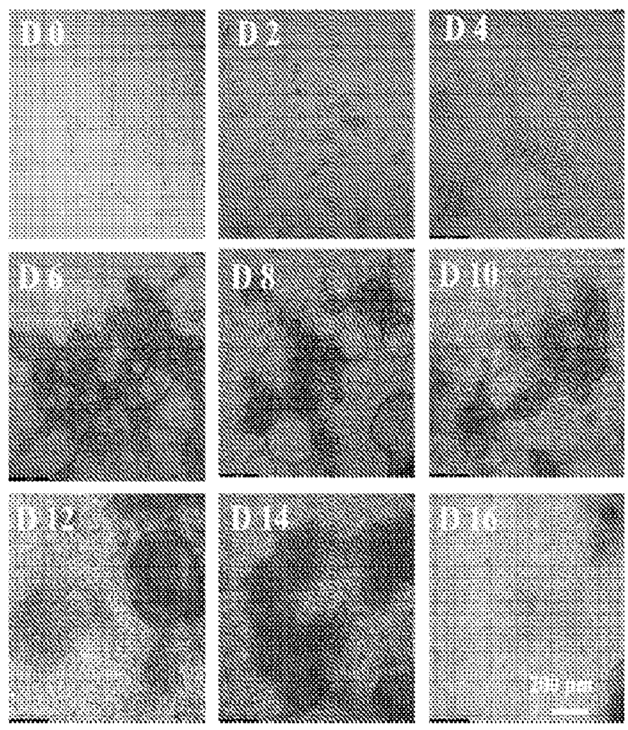
FIGS. 9A-9D. Robust AGM-like hematopoietic cell differentiation from various hPSC lines.
Figure 9B:
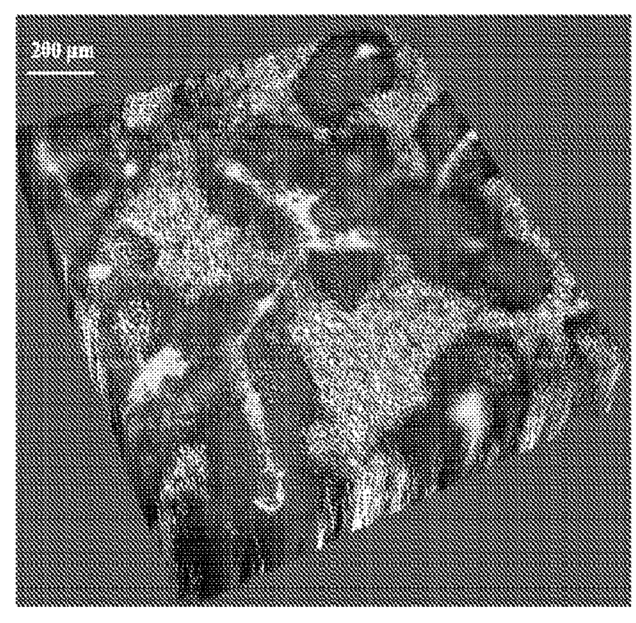

Chemically-defined conditions induce robust generation of AGM-like hematopoietic cells. Since the window for SB treatment is important for definitive hematopoiesis [8], we optimized the culture conditions for SB at the early hemogenic induction stage and found that day 4 to 6 treatment worked best to induce hematopoiesis (FIG. 8A), which resulted in more than 40% CD45+ hematopoietic cells on day 12. We also tested the effects of basal media on the hematopoietic cell differentiation at different stages in four cell culture media: Stemline II, LaSR basal medium [17], and DMEM medium plus 100 μg/mL ascorbic acid (DMEM/Vc) [18]) with or without 20% human AB serum (FIG. 8B). Our small molecule-based hematopoietic differentiation protocol worked well in most of the tested media, and the serum-containing medium outperformed all other conditions (FIG. 8C). While human serum (HS) significantly increased the purity of hematopoietic cells on day 12, the employment of undefined serum may increase the complexity and reduce the reproducibility. We thus employed the chemically-defined, serum-free combination as the differentiation medium (FIG. 4A), referring to hematopoietic cell generation from hPSCs as the GiTi (Gsk3 inhibitor, TGFβ inhibitor) protocol. The dynamic morphology changes were observed during GiTi differentiation along with the emergence of hematopoietic clusters from day 6 (FIGS. 9A-9B). Flow cytometry analysis also revealed dynamic changes of CD45, CD34 and SOX17 expression (FIG. 4B-D), with increasement of hematopoietic cells co-expressing CD34 and SOX17, and CD34 and CD45. The resulting cells were also positive for RUNX1 (FIG. 4E-F) that expresses in AGM-derived repopulating HSCs [34], confirming a definitive identity of our hematopoietic cells. Retrieval of SCF and FLT3L from the differentiation medium reduced both the yield and purity of CD45+ hematopoietic cells (FIG. 4G-H).

Figure 9C:
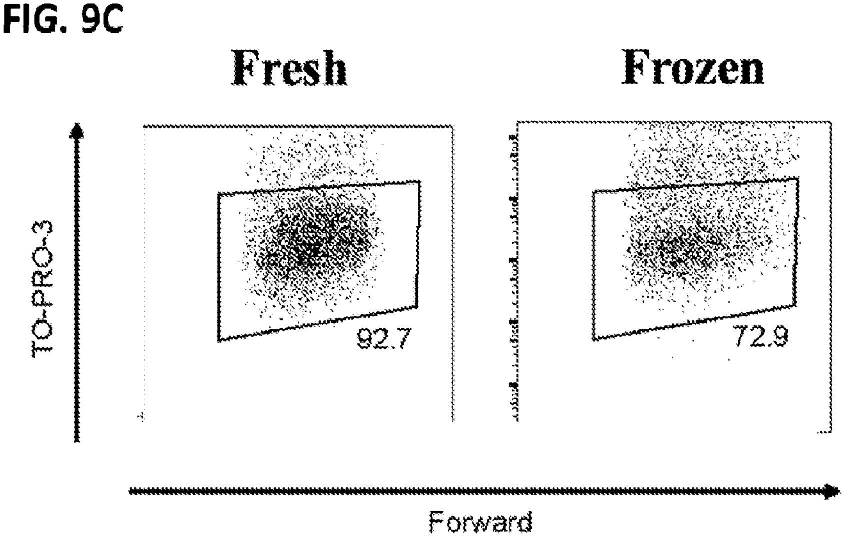
Figure 9D:
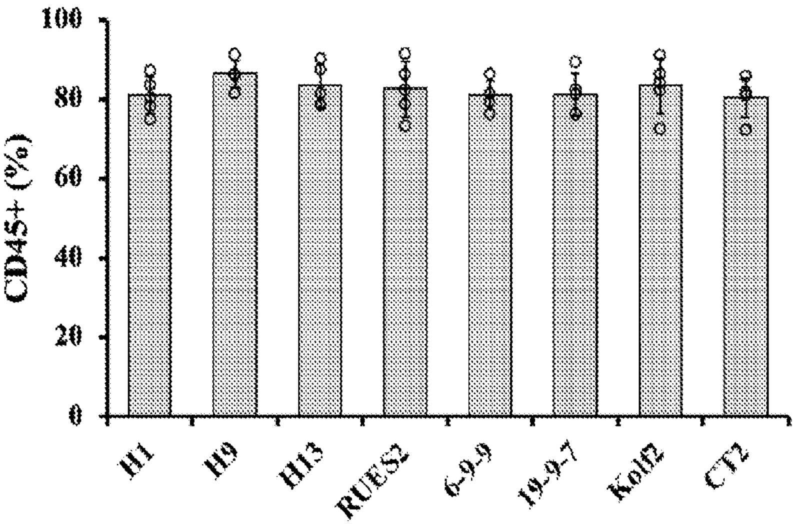

Importantly, the resulting hematopoietic cells have a high viability after the frozen-thawed process (FIG. 9C), indicating their potential for long-term storage and off-the-shelf application. Collectively, we developed a chemically-defined, feeder-free monolayer culture platform for the generation of homogenous AGM-like hematopoietic cells from 11 (9 normal and 2 genetically-modified) hPSC lines (FIG. 9D), highlighting its reproducibility and robustness.

Figures 5A, 5B, 5C, 5D:
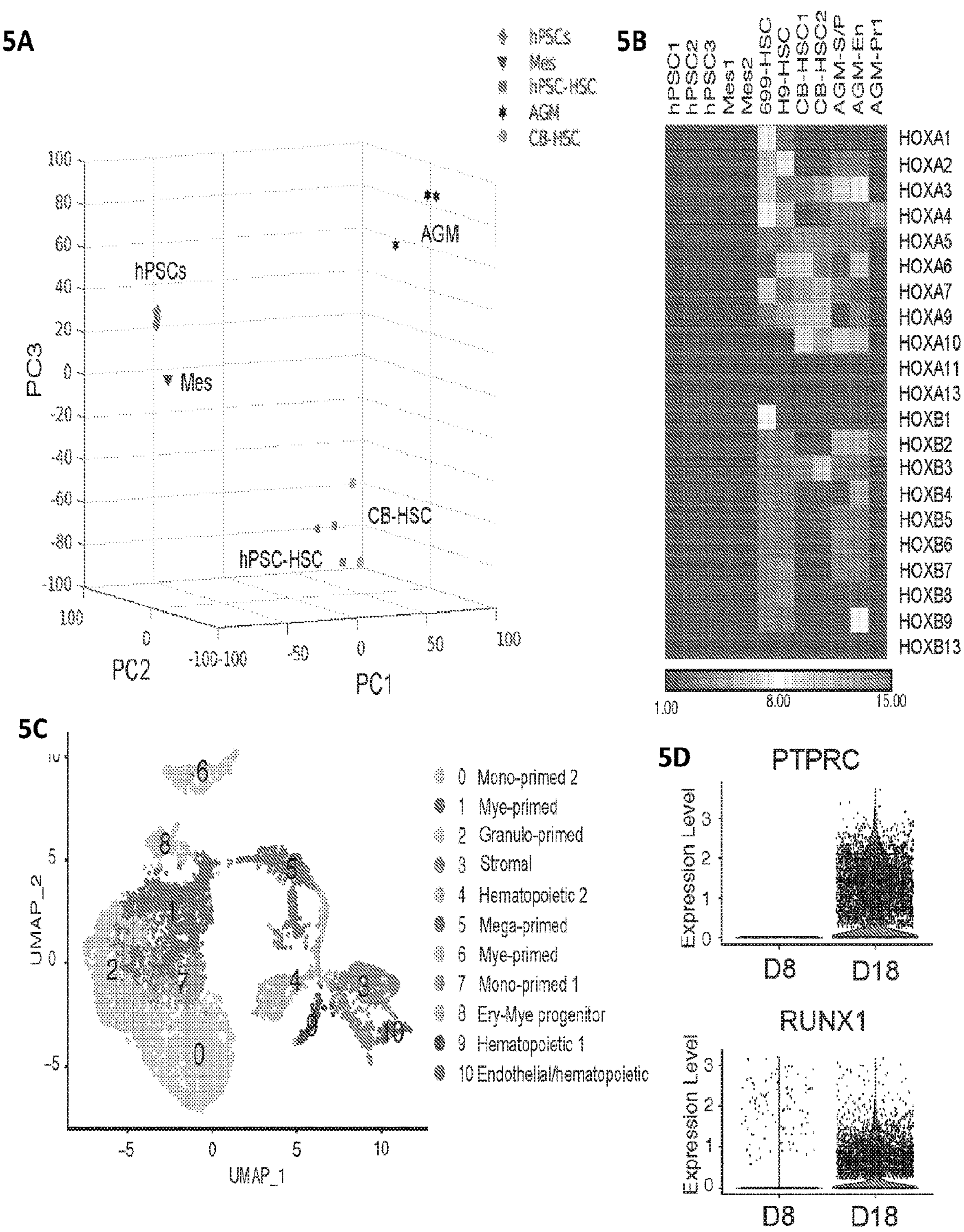
FIGS. 5A-5H. Transcriptome analysis of hPSC-derived definitive hematopoietic cells.
Figure 10A:
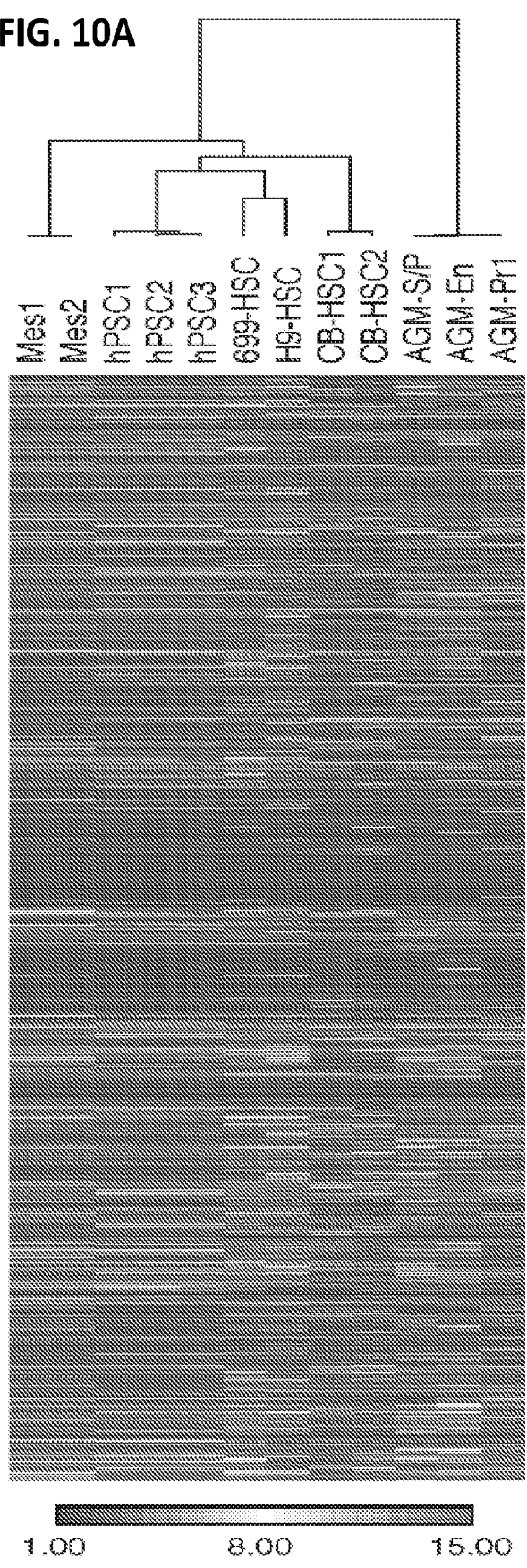
FIGS. 10A-10D. Transcriptional similarity among hPSC-derived, AGM and CB hematopoietic cells.

Transcriptome Analysis Reveals Global Similarity Between hPSC-Derived Hematopoietic Cells and Human AGM/Cord-Blood HSCs To further confirm the identity of hPSC-derived hematopoietic cells, RNA from 6-9-9 and H9 day 18 CD45+ hematopoietic cell differentiations were subjected to RNA sequencing (RNA-seq) analysis. Hierarchical clustering analysis (FIG. 10A) of RNA-seq expression data of hPSCs, hPSC-derived mesoderm (Mes), hematopoietic stem-like cells (HSCs), primary human neonatal cord-blood hematopoietic stem cells (CB-HSCs) [35], 5-week AGM endothelial (AGM-En), stem/progenitor (AGM-S/P), and progenitor 1 (AGM-Pr1) cells [10] showed that our hPSC-derived hematopoietic cells were closely related to primary cord-blood HSCs, indicating a more mature stage than that of the isolated AGM cells [10]. The close relationship of transcriptional signatures between hPSC-derived hematopoietic cells and CB-HSCs were also confirmed by principal component analysis (PCA) on the RNA-seq data (FIG. 5A). In the 3D score plot of the first three principal components (PCs), hPSC-derived hematopoietic cells clustered relatively closer to CB-HSCs and were distinct from other cell populations, including hPSCs and hPSC-derived mesoderm, from which they originated, as well as the AGM cells.

Figure 10B:
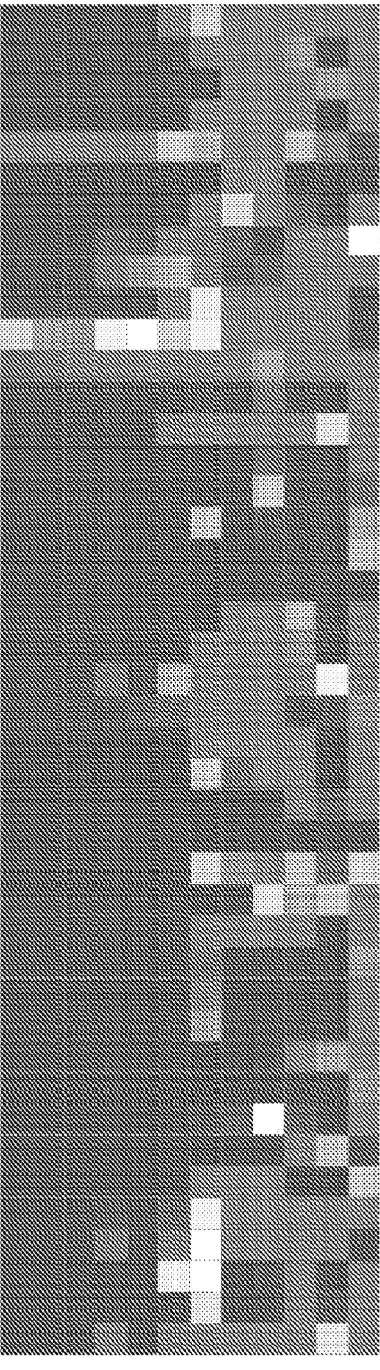
Figure 10C:
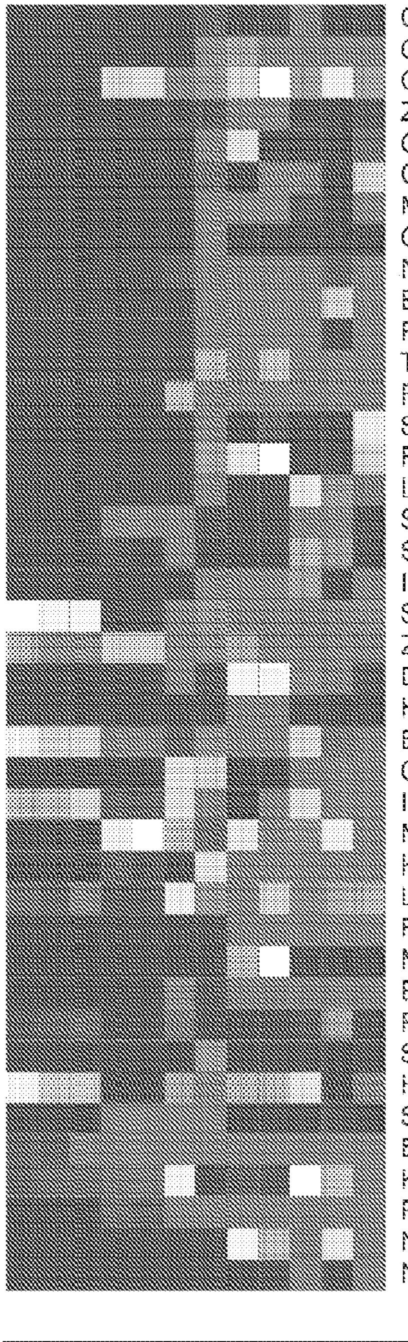
Figure 10D:
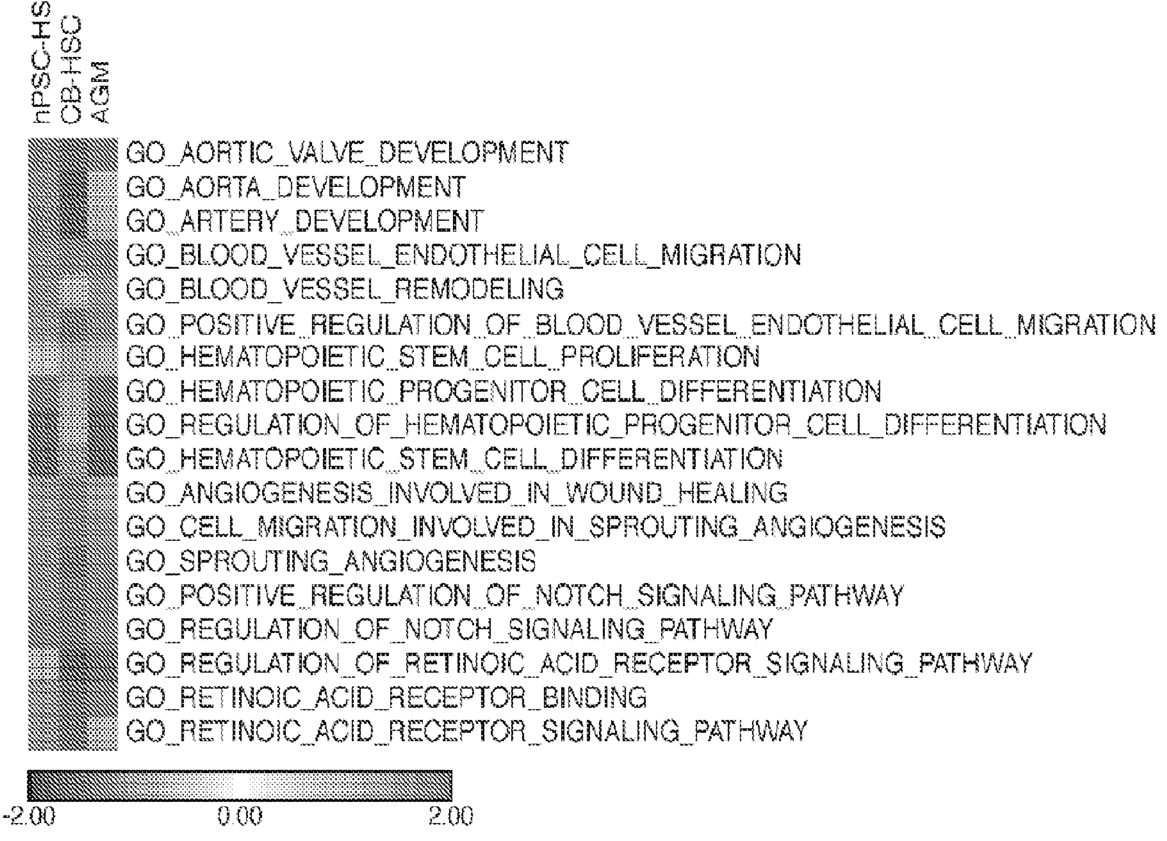

To further refine distinct transcriptional programs active during hematopoiesis, we examined specific hematopoietic genes among different hematopoietic cell populations. As expected, day 18 hPSC-derived cells shared expression of many hematopoietic transcription factors (FIG. 10B) and cell-surface markers (FIG. 10C) with AGM and CB cells, though mostly at lower expression levels. Gene set enrichment analysis (GSEA) over hPSCs identified enriched hematopoiesis-related gene ontology (GO), including “aorta development”, “cell migration”, “hematopoietic stem cell proliferation”, “Notch signaling regulation”, which further confirmed the transcriptional similarity between hPSC-derived and AGM cells (FIG. 10D). Importantly, very similar expression patterns of HOXA, a landmark of AGM hematopoiesis [10], and HOXB genes were observed in the day 18 hPSC-derived and AGM hematopoietic cells (FIG. 5B). Collectively, our data suggests the transcriptional similarity between our hPSC-derived cells and CB-HSCs, highlighting the definitive trajectory of our GiTi hematopoietic differentiation [7].

Figures 11D, 11E, 11F, 11G, 11H:
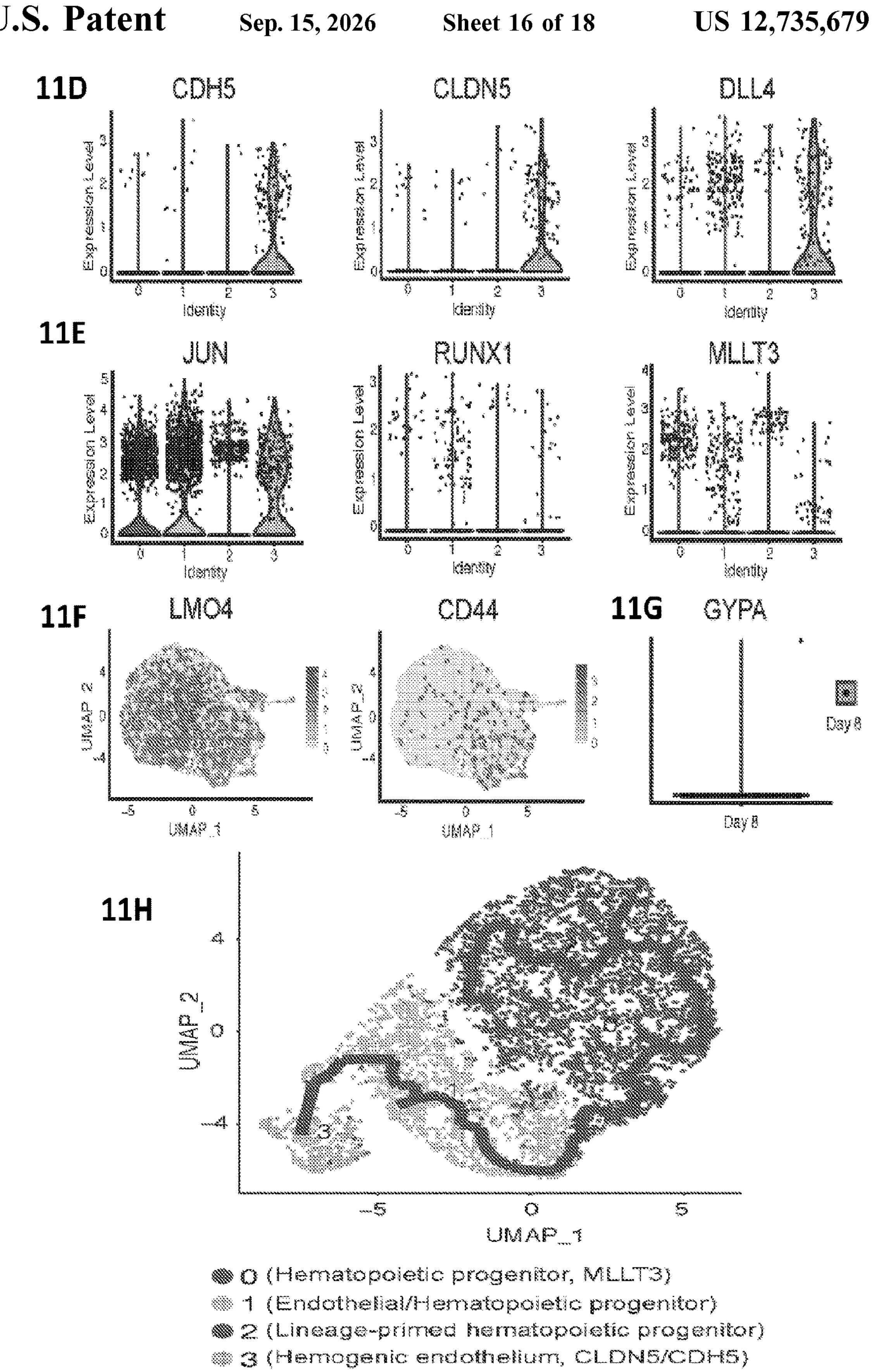

Single Cell RNA-Sequencing Analysis Identifies Discrete Sub-Populations in hPSC-Derived Hematopoietic Cells To investigate the dynamics and heterogeneity of hematopoietic cells emerged from hPSC-derived homogenous SOX17+CD34+HE, we performed scRNA-seq analysis on the day 8 (FIGS. 11A-11D) and day 18 (FIG. 5) suspension cells. UMAP embedding of scRNA-seq data revealed 4 distinct clusters and 11 different clusters of cells on day 8 (FIG. 11A) and 18 (FIG. 5C), respectively. As expected, day 18 cells expressed much stronger hematopoietic cell markers PTPRC (CD45) and RUNX1 (FIG. 5D). Cell identities in distinct clusters were assigned based on their enriched markers (FIGS. 11B-11D): clusters that expressed high levels of lineage markers were annotated as primed progenitors, whereas clusters annotated as progenitors only enriched in progenitor-associated genes. Day 8 cells included clusters of endothelial (CLDN5/CDH5), early (CAV1/RUNX1) hematopoietic, hematopoietic (MTTL3) [10] and lineage-primed hematopoietic progenitors that enriched in mitochondrial genes [36] (FIGS. 11B-11D). Day 18 cells contained clusters of stromal (IGF2/COL1A1), endothelial, and hematopoietic cells, as well as clusters of progenitor cells primed towards megakaryocyte (GP9/PF4), monocyte (SPP1/CCL3 and CD74/MMP9), granulocyte (AZU1/PRTN3), myeloid (MPO/LYZ) and erythroid (KLF1/HBE1) [10]. Interestingly, hematopoietic cells under current culture condition was biased to granulocytes other than erythroid lineages since much less cells enriched for HBElor KLF1 expression [37] were detected, indicating their definitive identity [38]. Both day 8 and 18 cells displayed high expression levels of definitive AGM hematopoiesis markers LMO4 and CD44 [39,40] (FIG. 5E, 11E), while only a few cells in both samples were positive for the primitive marker GYPA (CD235$\alpha$) [24] (FIG. 11F), further supporting their definitive identity. The observed downregulation of LMO4 and upregulation of CD44 upon EHT was consistent with previous in vivo emergence of hematopoietic cells from aortic endothelium of mouse AGM [39]. In addition to its role in regulating EHT, CD44 is also a maker of adult HSCs [41], and involved in fetal HSC homing and long-term engraftment [42], suggesting a potentially high homing ability of our hPSC-derived hematopoietic cells.

Figures 5E, 5F, 5G, 5H:
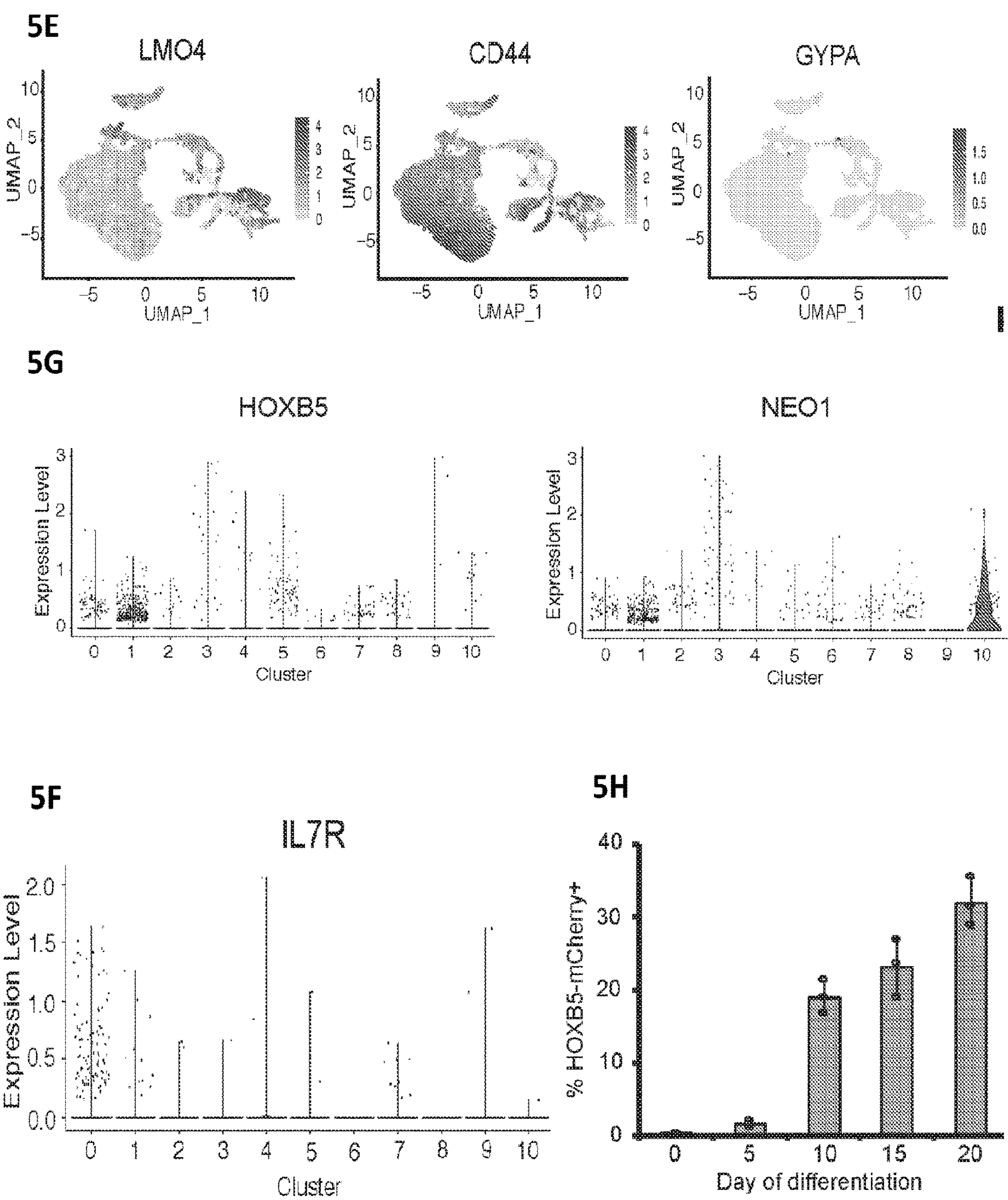
Figures 12A, 12B, 12C, 12D:
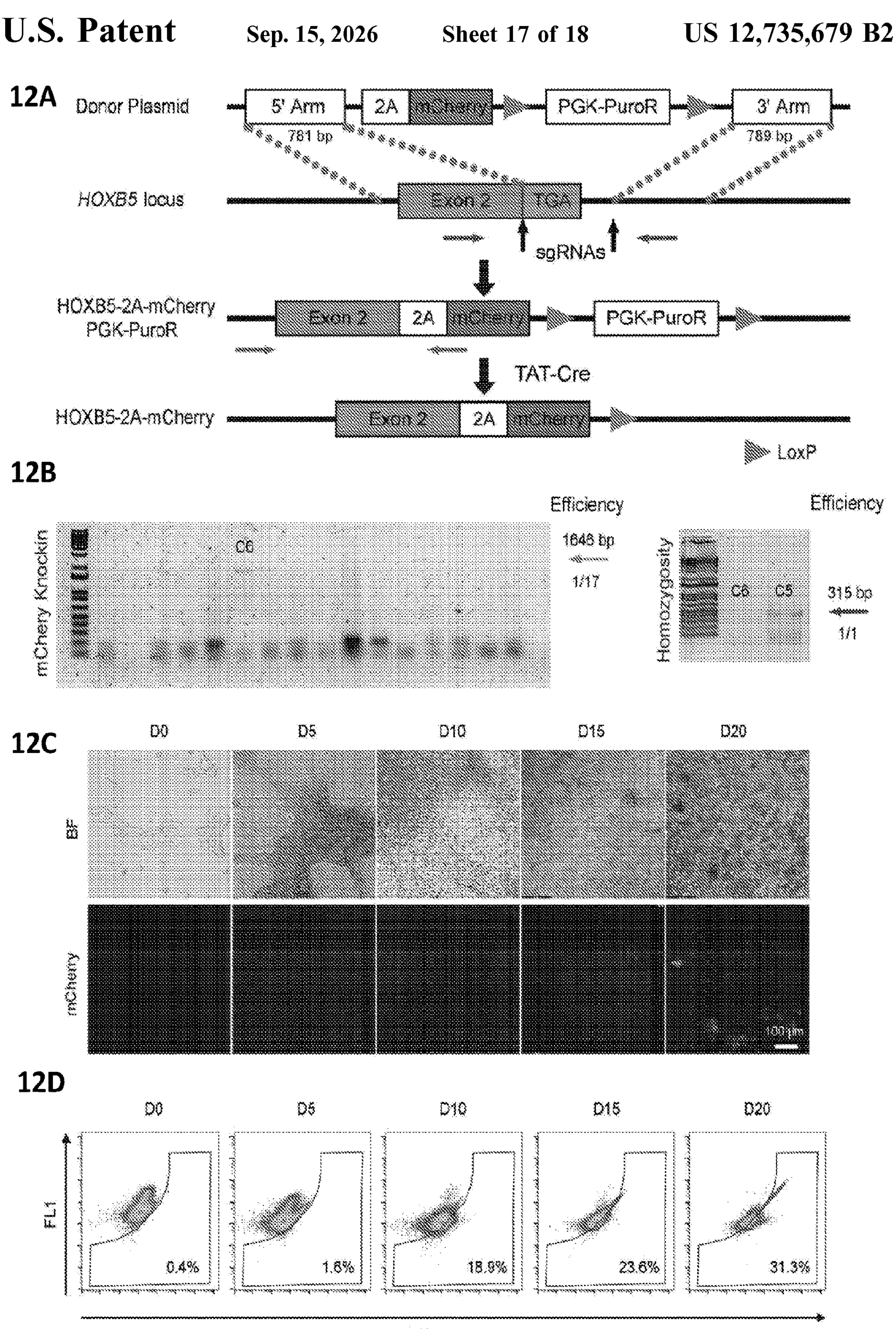
FIGS. 12A-12D. Construction of VEcad-eGFP HOXB5-mCherry dual reporter H9 hPSC line using Cas9 nuclease.

To study the hierarchy of our hematopoietic cell populations, trajectory analysis was performed using the Monocle packages [43]. Single-cell trajectory analysis on day 8 cells clearly demonstrated emergence and development of hematopoietic cells from hemogenic endothelium (FIG. 11G). For day 18 cells, hematopoietic progenitor cells branched from a central core to three distinct trajectories of monocyte-, granulocyte- and erythroid/megakaryocyte-primed lineages. Additional endothelial (CAV1), hematopoietic (RUNX1), erythroid (KLF1/HBE1), and T-cell progenitor (IL7R) cells [44] were also positioned to the trajectory map and represented by distinct branches (FIG. 5F). The high expression of HOXB clusters (FIG. 5B) may suggest the existence of potential long-term (LT) HSCs in hPSC-derived cells, since HOXB cluster genes were predominantly enriched in murine LT HSCs [45]. Particularly, HOXB5 [46] and NE01 [47] was recently reported as makers of murine LT-HSCs. The expression of HOXB5 and NE01 was detected across different early or lineage-primed hematopoietic cells via scRNA-seq analysis (FIG. 5G). To better monitor the dynamic expression of HOXB5 during hematopoietic cell differentiation, we knocked the mCherry fluorescent protein into the endogenous HOXB5 locus of H9 VE-cad-eGFP reporter line via CRISPR/Cas9-mediated homology-directed repair (HDR) [48] (FIG. 12A). After puromycin (Puro) selection, PCR genotyping and sequencing showed that 1 out of 17 picked clones was successfully targeted in both alleles (FIG. 12B). The homozygous clone was then applied to GiTi hematopoietic differentiation, and the mCherry signal was first detected at day 5 and elevated at day 20 (FIGS. 5H, 12C-12D), demonstrating the presence of potentially long-term repopulating HOXB5+ hematopoietic cells. Collectively, our data revealed the heterogeneity and hierarchy of seemingly homogenous AGM-like cells, highlighting the definitive trajectory of our GiTi hematopoietic differentiation [7].

In Vitro and In Vivo Characterization of hPSC-Derived AGM-Like Hematopoietic Cells To further assess their hematopoietic potential, we performed lymphoid and myeloid analysis on day 15 hPSC-derived cells. Methycellulose-based colony-forming unit assays resulted in the formation of erythroid (CFU-E), granulocyte/macrophage (CFU-GM), macrophage (CFU-M), and multilineage progenitor (CFU-GEMM) colonies (FIGS. 13A-13C), confirming the erythroid and myeloid potential of our hPSC-derived cells. We next assessed their potential for T and natural killer (NK) cell generation on OP9-DLL4 feeder cells [49], since the ability to produce lymphocytes is a hallmark of definitive hematopoiesis [24]. After 4 weeks, more than 15% of CD4+CD8+T (FIG. 6A) and 85% CD45+CD56+NK cells (FIG. 6B) were obtained in the co-culture differentiation, demonstrating that our hPSC-derived hematopoietic cells are able to produce immune cells for both research and clinical applications.

Figures 6A, 6B, 6C, 6D, 6E, 6F:
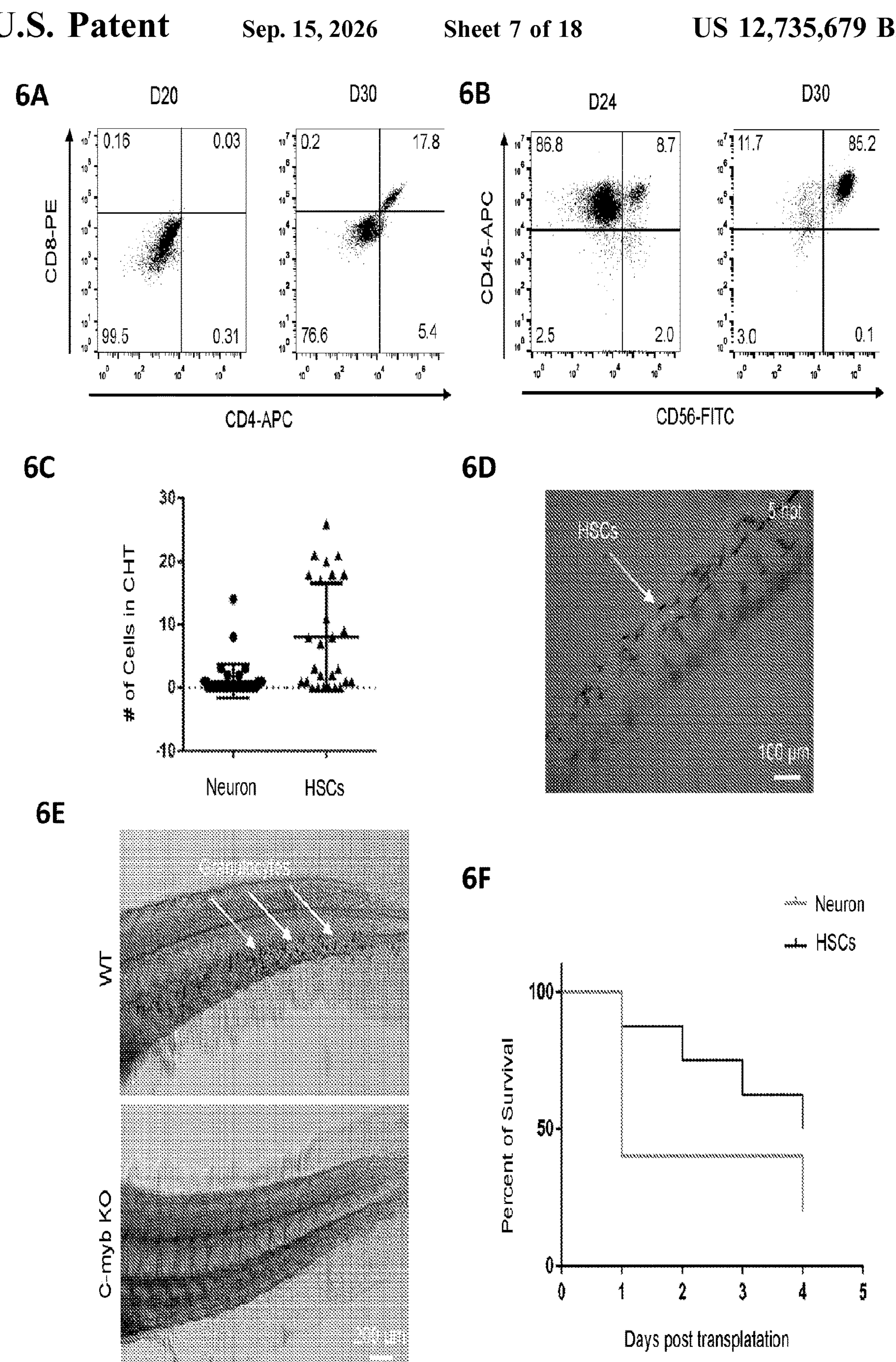
FIGS. 6A-6F. In vitro and in vivo characterization of hPSC-derived AGM-like hematopoietic cells.
Figures 13A, 13B, 13C, 13D, 13E, 13F, 13G:
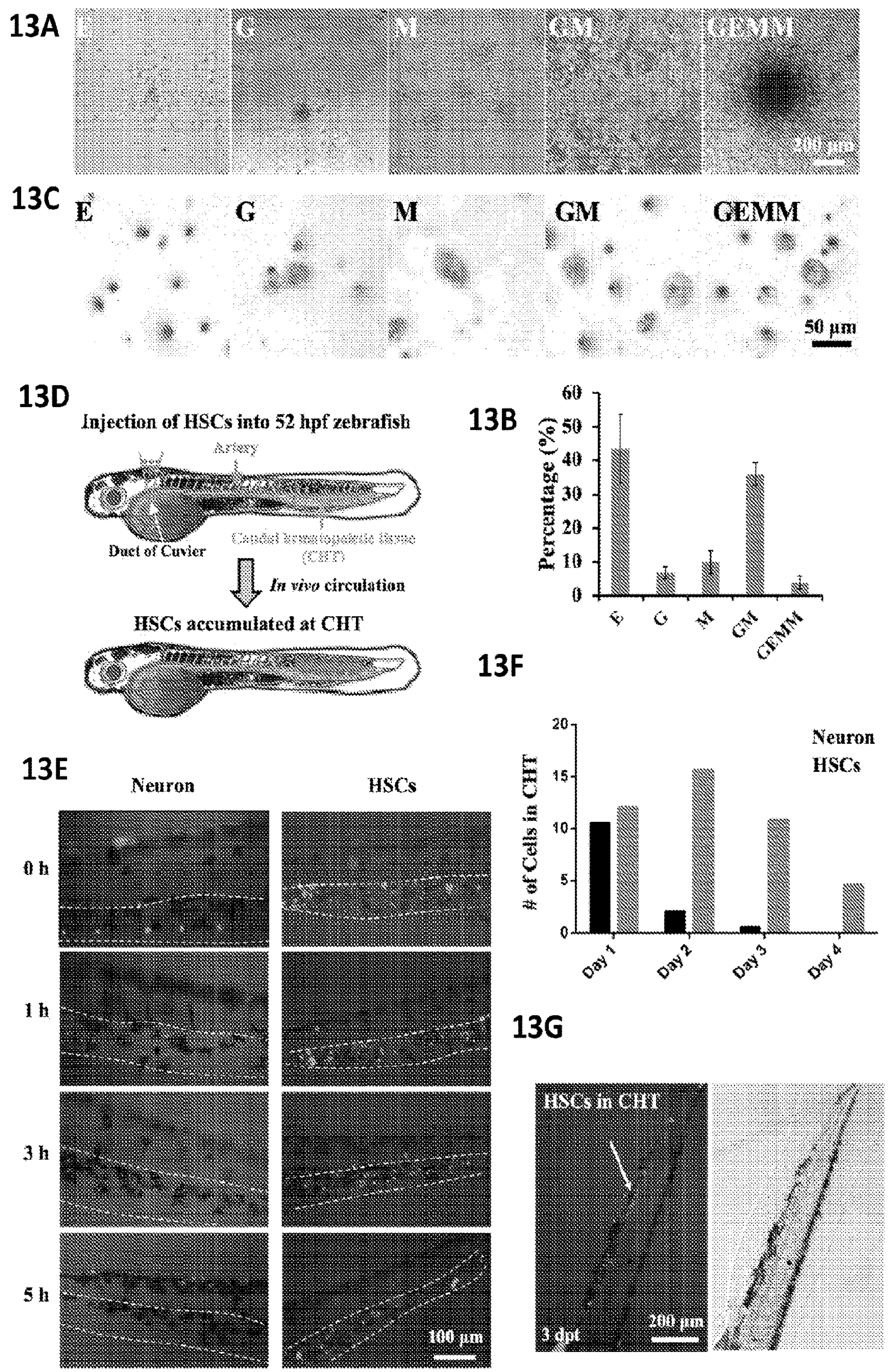
FIGS. 13A-13G. In vitro and in vivo functional characterization of hPSC-derived AGM-like hematopoietic cells.

LT-HSCs [50] and hPSC-derived AGM-like cells [10] could home to bone marrow after tail vein injection. To examine their homing ability, about 200 purified mCherry+ CD45+ of hPSC-derived hematopoietic cells were injected in the duct of Cuvier of 48-hr old zebrafish (FIG. 13D) [51,52]. mCherry+ hematopoietic cells were observed in the zebrafish caudal hematopoietic tissue (CHT) as soon as 1-hour post-transplantation (hpt) (FIG. 13E). As compared to hPSC-derived neuron cells, more hematopoietic cells were homed to CHT at 5 hpt (FIGS. 6C-6D). We also injected the mCherry+CD45+ hematopoietic cells directly into the blastoderm of c-myo knockout (FIG. 6E) bloodless zebrafish embryos at 3-5 hours post-fertilization (hpf), and mCherry+ hematopoietic cells, but not neurons, were observed in the CHT region up to 4 days post-transplantation (dpt) (FIGS. 13F-13G). Importantly, the hPSC-derived hematopoietic cells significantly rescued the bloodless fish up to 4 days after transplantation (FIG. 6F), highlighting their homing and rescuing abilities. Collectively, our results demonstrated the function of hPSC-derived AGM-like cells, though further investigations of their long-term repopulating ability are needed.

Figure 7:
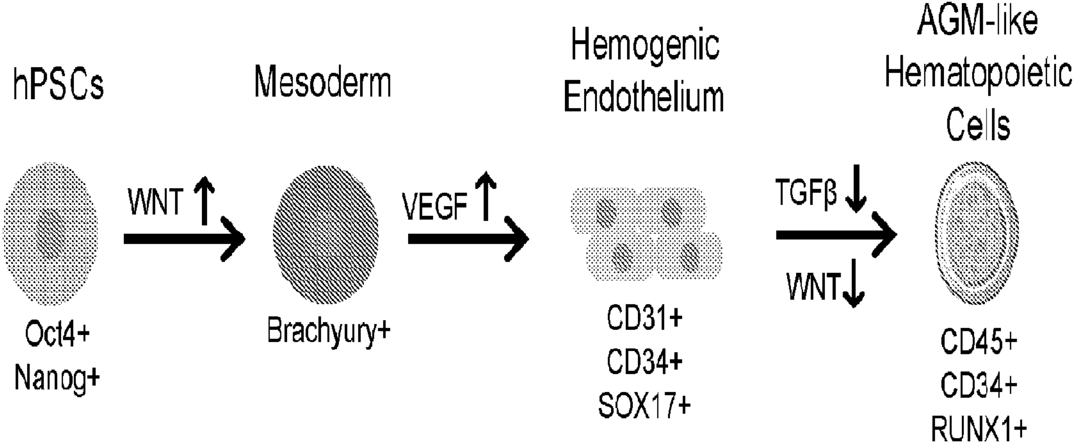
FIG. 7. A schematic model highlighting the specification of hPSCs to AGM-like hematopoietic cells by stage-specific modulation Wnt, VEGF and TGFβ signaling.

While attempts have been made to develop human hematopoietic cell differentiation protocols from hPSCs with stage-specific employment of morphogens by recapitulating in vivo hematopoiesis, it remains unknown which developmental signaling pathways are sufficient and essential to specify human AGM-like hematopoietic cells, the first wave of LT-HSCs. In addition, strategies for efficient, cost-effective generation of homogenous AGM-like cells are still lacking, limiting their large-scale production for both clinical and research applications. This study demonstrates robust and efficient generation of homogenous AGM-like hematopoietic cells from multiple hPSC lines via sequential manipulation of Wnt and TGFβ signaling under chemically-defined and xeno-free conditions (FIG. 7). Importantly, we also showed that stage-specific manipulation of Wnt signaling alone is sufficient to induce homogenous AGM-like SOX17+ hemogenic endothelium and hematopoiesis from hPSCs, further demonstrating the important role of Wnt signaling during multiple stages of definitive hematopoiesis [10,24,30].

This study also demonstrates transcriptional and functional similarity among hPSC-derived, primary AGM and CB hematopoietic cells. At global levels, hPSC-derived hematopoietic cells clustered closer to CB-HSCs than AGM cells, reflecting distinct developmental stages of the collected hPSC-derived and AGM cells. Further examination of specific hematopoietic genes and ontology confirmed the transcriptional similarity between hPSC-derived and AGM cells. Notably, very similar patterns of HOXA cluster gene expression was observed between them, highlighting their potential for repopulating HSC generation [10]. In addition, our hPSC-derived AGM-like hematopoietic cells presented lymphoid and myeloid potential in vitro, and homed to fish caudal hematopoietic tissue (CHT) in vivo and rescued bloodless zebrafish after transplantation. It will also be interesting to investigate whether our hPSC-derived hematopoietic cells could home and repopulate the bone marrow in murine models. Recent work has successfully demonstrated the homing capacity of hPSC-derived AGM-like cells, but failed to show evidence of their long-term repopulating ability, which is likely due to the incorrect expression pattern of HOXA genes [10]. Although similar pattern was observed, the expression of HOXA genes did not reach an AGM cell expression level in our hPSC-derived cells. Additional maturation strategies, such as co-culture with OP9 feeder cells [53-55] and RA patterning [10], may be required for hPSC-derived AGM-like cells to achieve long-term repopulating capacity.

Collectively, our data establishes a simplified, novel in vitro model (FIG. 7) of human definitive hematopoiesis in which small molecule-mediated exogenous modulation of Wnt signaling with or without TGFβ crosstalk is sufficient for the specification of hematopoietic cells from hPSCs. This finding is consistent with a previous report that retinoic acid signaling-mediated Wnt inhibition is essential for HSC development from hemogenic endothelium in mice [30]. This completely defined, xeno-free hematopoietic differentiation platform could be harnessed to efficiently and massively produce hematopoietic cell lineages, including blood and immune cells, from hPSCs, and provide insights into molecular mechanisms of hematopoietic development and accessible cell source for treating blood diseases and cancer.

Materials and Methods

Maintenance and Differentiation of hPSCs.

19-9-11, 19-9-7, 6-9-9, H1, H9 and H13 were obtained from WiCell and maintained on Matrigel- or iMatrix 511-coated plates in mTeSR plus or mTeSR1 medium according to a previously published method [56]. RUES2 were kindly provided by Dr. Ali H. Brivanlou at the Rockefeller University. The Kolf2 and CT2 data were acquired in Dr. Yang Yang's lab and Dr. Ourania Andrisani's lab at Purdue. H9 7TGFβ Wnt reporter and 19-9-11 ischcat-1 as well as ischcat-2 lines [33] were kindly provided by Dr. Sean Palecek at University of Wisconsin-Madison. To make hematopoietic cells, hPSCs were dissociated with 1 mM EDTA and seeded onto iMatrix 511 or Matrigel-coated 6-, 12- or 24-well plate at a cell density between 10,000 and 80,000 cell/$cm^2$ in mTeSR plus or mTeSR1 medium with 5 μM Y27632 for 24 hours (day-1). At day 0, cells were treated with 6 μM CHIR99021 (CHIR) in DMEM medium supplemented with 100 ug/ml ascorbic acid (DMEM/Vc) [18], followed by a medium change with LasR basal medium at day 1, day 2 and day 3. For female hPSC lines [57], 50 ng/mL VEGF was added to the medium from day 2 to day 4. At day 4, medium was replaced by Stemline II medium (Sigma) supplemented 10 μM SB431542. After 2 days, SB431542-containing medium was aspirated and cells were maintained in Stemline II medium with or without 50 ng/mL SCF and FLT3L. At day 9 and every 2 to 3 days afterwards, aspirate half medium and add fresh Stemline II medium with or without SCF/FLT3L until analysis. Other media used to induce hematopoietic cells were illustrated in FIG. 8B.

Genome Editing of hPSCs.

Two Cas9 sgRNAs targeting near the HOXB5 stop codon (1: GGCTCCTCTGGGCGGGCTCAGGG (SEQ ID NO: 1) and 2: ATCGTAACACAAGGCGAGGC AGG (SEQ ID NO: 2) with a G added at the beginning) were used. To generate the HOXB5-2A-mCherry donor plasmid, DNA fragments of about 800 bp in length were PCR amplified from genomic DNA before and after the stop codon of HOXB5 and were cloned into the VE-cad-2A-eGFP (Addgene #92309) and VE-cad-2A-mCherry (Addgene #31938) donor plasmids replacing the VEcad homologous arms. The resulting 3 μg gRNA1, 3 μg gRNA2, and 6 μg VEcad-2A-mCherry donor plasmids were prepared in 100 μl stem cell nucleofection solution (Lonza, #VAPH-5012) and then co-nucleofected into 2.5-3 million singularized H9 hPSCs pretreated with 5 μM Y27632 overnight using program B-015 in a Nucleofector 2b. The nucleofected cells were subsequently plated onto one well of a Matrigel-coated 6-well plate in 3 mL pre-warmed mTeSR plus with 10 μM Y27632. Twenty-four hours later, and every day afterward, the medium was changed with fresh mTeSR plus. Once cells are confluent, 1 μg/ml puromycin was added to the mTeSR plus for selection for about 2 weeks. Single cell clones were then picked into wells of a Matrigel-coated 96-well plate and subjected to PCR genotyping after 4-7 days. To generate an inducible gene knockdown system in hPSCs, RfxCas13d [58,59] (Addgene #138147) was PCR amplified and cloned into our all-in-one PiggyBac (PB) backbone [60] by replacing SARS-CoV2 N gene (Addgene #154399). The U6 driven construct, containing a 5' direct repeat 30 (DR30) and a BbsI-based single guide RNA (sgRNA) cloning site, was then cloned right before the 3' PB sequence (FIG. 1E), leading to an all-in-one PB inducible Cas13d-mediated gene knockdown plasmid (Addgene #155184). The SOX17 targeting sgRNA1 and sgRNA2 were designed using an online tool (https://cas13design.nygenome.org/) and cloned into the Cas13d backbone to make SOX/7 targeting plasmids (Addgene #155187 and #155188). To generate inducible β-catenin overexpression plasmids, the eGFP gene (Addgene #96930) was replaced by the E[beta]P gene [61] (Addgene #24313) and led to the XLone-BSD β-catenin plasmid. The SOX17 knockdown or β-catenin overexpression plasmids were then used to transfected H9 hPSCs along with hyPBase plasmid via Lipofectamine Stem (ThermoFisher) according to the manufacturer's instructions. Once transfected cells were confluent, 5 μg/ml puromycin or 20 μg/ml blasticidine (BSD) were used to select the drug-resistant hPSCs for one or two days, and the drugs were reapplied to the survived cells once they recovered and used consistently to maintain the engineered H9 hPSCs to avoid gene silencing during differentiation.

Hematopoietic Colony Forming Assay and Wright-Giemsa Staining.

About $10^4$ day 15 hPSC-derived hematopoietic cells were grown in 1.5 ml cytokine containing MethoCult H4434 medium (StemCell Technologies, Vancouver) at 37° C. After 14 days, the hematopoietic colonies were scored for colony-forming units (CFUs) according to cellular morphology. Hematopoietic cells were also seeded onto glass slides and stained with modified Wright-Giemsa stain solution.

NK and T Cell Differentiation from Hematopoietic Cells.

Both NK [49] and T [62] cell differentiations were performed on OP9-DLL4 feeder layer (kindly provided by Dr. Igor Slukvin at University of Wisconsin Madison) in α-MEM medium supplemented with 20% FBS and 1% GlutaMAX. To initiate NK cell induction, day 15 hematopoietic cells were cultured on OP9-DLL4 with 100 ng/mL FLT3L, 5 ng/mL IL-7, 40 ng/mL SCF, and 35 nM UM171. After 7 days and every 7 day afterwards, cells were transferred to fresh OP9-DLL4. After 14 to 21 days, floating cells were collected and subjected to flow cytometry analysis. Similar approach was used to induce T cell differentiation on OP9-DLL4, except different cytokines were used: 10 ng/ml SCF, 5 ng/mL IL-7 and Flt3L.

Flow Cytometry Analysis.

Floating hematopoietic cells were gently pipetted and filtered through a 70 or 100 μm strainer sitting on a 50 ml tube. The cells were then pelleted by centrifugation and washed once in PBS−/−solution with 1% bovine serum albumin (BSA). The cells were stained with appropriate conjugated antibodies (Table 1) for 25 mins at room temperature in dark, and analyzed in Accuri C6 plus flow cytometer (Beckton Dickinson) after washing once with BSA-containing PBS−/−solution. FlowJo software was used to process collected flow data.

Bulk RNA Sequencing and Data Analysis.

Total RNA of day 18 hPSC-derived CD45+ hematopoietic cells was prepared with the Direct-zol RNA MiniPrep Plus kit (Zymo Research) according to the manufacturer's instructions. Samples were performed in Illumina HiSeq 2500 by GENEWIZ. HISAT2 program [63] was employed to map the resulting 2×150 sequencing reads to the human genome (hg 19), and the python script rpkmforgenes.py [64] was used to quantify the RefSeq transcript levels (RPKMs). The original fastq files and processed RPKM text files were submitted to NCBI GEO (GSE155196). RNA-seq data of human primary AGM and neonatal cord blood HSC samples were retrieved from NCBI (SRR3475781, 3475782, 3475783 [10], 3039602, and 3039608 [35]). Hierarchical clustering of whole transcripts and heatmap of hematopoietic-specific genes were then plotted using Morpheus (Broad Institute). Principal component analysis (PCA) was processed in R program and 3D score plot of the first three principal components (PCs) was plotted in MATLAB. GSEA software (Broad Institute) was used to perform gene ontology (GO) enrichment analysis and the values of normalized enrichment score (NES) were used to plot GO heatmap in Morpheus.

Single-Cell RNA Sequencing (scRNA-Seq) Analysis.

As previously described [65], scRNA-seq was performed using the 10×Genomics 3' v3 kit, following their protocol targeting recovery of 10,000 cells. Libraries were constructed per the manufacturer's instructions and sequenced using Illumina's NovaSeq 6000 platform in the Center for Medical Genomics at Indiana University. Average read depth across the samples was 43,000 reads/cell. Reads were then aligned to the human genome GRCh38/hg38 using the CellRanger 2.1.0 software. Subsequent analysis was performed in R using the filtered barcode and count matrices produced by CellRanger. Seurat 3.1.0 was used to analyze the single-cell data [66]. All time-points were initially merged together and filtered for quality control parameters. Seurat's SCTransform function was used to normalize and scale the data to minimize batch effects. Dimensionality reduction was performed through Principal Component Analysis (PCA) following Seurat's tutorial as evaluated by elbow plots. UMAP embedding parameters were based on the top 30 PCs and embedded in 2-dimensions for visualization. Seurat's FindAllMarkers function was used to identify differentially expressed genes (DEGs) per cluster and then manually annotated based on enriched gene expression. All genes considered for cell-type classification had a P-value of less than 0.0001 using a Mann-Whitney Wilcoxon test. Monocle version 2 and 3 were used for pseudotime analysis and trajectory inference [43].

The resulting scRNA-seq raw and processed data can be accessed via GEO with accession number: GSE155196.

RT-PCR Analysis.

Cells cultured on 24-well plate were collected and lysed in 500 μL TRIzol™ reagent (Invitrogen). Total RNA were then prepared with the Direct-zol RNA miniprep kit (Zymo) with in-column DNase treatment following the manufacture's instruction. cDNA was reverse transcribed from 1 μg RNA with ProtoScript First Strand cDNA Synthesis Kit (NEB) and used for RT-PCR with GoTaq Green Master Mix (Promega). GAPDH was used as an endogenous housekeeping control and the primer pairs for targeted genes were listed in Table 2.

TABLE 1

Antibodies used in this study.

| Antibody | Source/Isotype/clone/cat. no. | Concentration |
|---|---|---|
| CD43-APC | BD Biosciences/Mouse IgG1/1G10/560198 | 1:50 |
| CD45-PE | BD Biosciences/Mouse IgG1/HI30/555483 | 1:50 |
| CD45-APC | BD Biosciences/Mouse IgG1/HI30/555485 | 1:50 |
| CD45-FITC | Biolegend/Mouse IgG1/HI30/304006 | 1:50 |
| CD34-FITC | Miltenyi Biotec/Mouse IgG2a/AC136/130-113-178 | 1:50 |
| CD34-APC | Miltenyi Biotec/Mouse IgG2a/AC136/130-113-176 | 1:50 |
| SOX17-APC | R&D Systems/Goat IgG/IC1924A | 1:50 |
| CD4-APC-Cy7 | BD Biosciences/Mouse IgG1/RPA-T4/561839 | 1:50 |
| CD8-PE | BD Biosciences/Mouse IgG1/RPA-T8/555367 | 1:50 |
| CD56-APC | BioLegend/Mouse IgG1/5.1H11/362503 | 1:50 |
| VE-cadherin | Santa Cruz/Mouse IgG1/F-8/sc9989 | 1:200 |
| CD31-FITC | Miltenyi Biotec/Mouse IgG1/AC128/130-117-539 | 1:50 |
| CD31-APC | Miltenyi Biotec/Mouse IgG1/AC128/130-119-976 | 1:50 |
| CD31-APC | eBioscience/Mouse IgG1/WM-59/17-0319-42 | 1:100 |
| CD235a-FITC | BD Biosciences/Mouse IgG2b/GA-R2/561017 | 1:50 |
| RUNX1-Alexa 488 | Abcam/Rabbit IgG/EPR3099/ab199221 | 1:200 |
| Secondary Antibody | Alexa 488 Goat anti-Ms IgG1/A-21121 | 1:1,000 |
| Secondary Antibody | Alexa 488 Goat anti-Rb IgG/A-11008 | 1:1,000 |
| Secondary Antibody | Alexa 594 Goat anti-Ms IgG2b/A-21145 | 1:1,000 |
| Secondary Antibody | Alexa 594 Goat anti-Ms IgG/A-21145 | 1:1,000 |
| Secondary Antibody | Alexa 594 Goat anti-Rb IgG/A-11012 | 1:1,000 |
| Secondary Antibody | Alexa 647 Goat anti-Rb IgG/A-21244 | 1:1,000 |

TABLE 2

Oligonucleotide primers used in this study.

| SEQ ID NOs | Genes | Sequences (5'-3') | Size (bp)/ Tm (° C.)/ Cycles |
|---|---|---|---|
| 3 | AXIN2 | F: CTCCCCACCTTGAA TGAAGA | 211/60/35 |
| 4 | WNT3A | F: GCCCCACTCGGATA CTTCT | 189/58/40 |
| 5 | CTNNB1 | F: GAATGAGACTGCTG ATCTTGGAC | 250/58/30 |
| 6 | GATA2 | F: GCAACCCCTACTAT GCCAAC | 212/60/40 |
| 7 | AFP | F: AAATGCGTTTCTCG TTGCTT | 136/60/35 |
| 8 | ALB | F: GCACAGAATCCTTG GTGAACAG | 101/61.8/35 |
| 9 | GAPDH | F: CCCCTTCATTGACC TCAACTACA | 342/58/30 |
| 10 | HOXB5 KI (Red) | F: CGGCTCTTACGGCT ACAATTA | 1646/60/42 |
| 11 | HOXB5 KI (Blue) | F: CCCCTTCATTGACC TCAACTACA | 342/58/30 |

TABLE 2-continued

Oligonucleotide primers used in this study.

| SEQ ID NOs | Genes | Sequences (5'-3') | Size (bp)/ Tm (° C.)/ Cycles |
|---|---|---|---|
| 12 | HOXB5 Cas9 gRNA1 | F: CACCGGCTCCTCTG GGCGGGCTCA | Annealing Oligoes |
| 13 | HOXB5 Cas9 gRNA2 | F: CACCGATCGTAACA CAAGGCGAGGC | Annealing Oligoes |
| 14 | iscramble Cas13d gRNA | F: AAACGGGTCTTCGA GAAGACCT | Annealing Oligoes |
| 15 | SOX17 Cas13d gRNA1 | F: AAACACCATAAATT ATATGCCAACACA | Annealing Oligoes |
| 16 | SOX17 Cas13d gRNA2 | F: AAACTAAGATTACT TGAAGTAGGCTCA | Annealing Oligoes |

Transplantation of hPSC-Derived Hematopoietic Cells into Zebrafish.

About 200 mCherry+CD45+ of hPSC-derived hematopoietic cells were injected in the duct of Cuvier of 48-hr old zebrafish [51,52]. After 1-, 3- and 5-hour post-transplantation (hpt), mCherry+ cells homed to CHT were recorded and quantified under fluorescent microscope mCherry+ hematopoietic cells. hPSC-derived neuron cells were used as a negative control. For the embryo injection into c-myb bloodless zebrafish [67], ~2,000 cells were microinjected directly into the blastoderm of 3- to 5-hpf zebrafish blastula.

At 1, 5, 48, 72 and 96 hpf, mCherry+ cells homed to CHT were recorded under fluorescent microscope and viable zebrafish were counted.

Some essential materials used in the culture and differentiation of stem cells are provided below. Part A: Cell culture medium. Human pluripotent stem cell (hPSCs) culture and maintenance media: media used for the general culture and expansion of hPSCs before differentiation, and any of the following 6 media (or any other similar commercial media) could be used for maintaining hPSCs used in this disclosure. mTeSR1: StemCell Technologies, 85850; mTeSR Plus: StemCell Technologies, 05825; Essential 8 Medium: ThermoFisher, A1517001; StemFlex Medium: ThermoFisher, A3349401; NutriStem hPSC XF Medium: Biological Industries, 05-100-1A; House-made LaSR medium (patented by our collaborator): Advanced DMEM/F12 (ThermoFisher cat. 12634-028), 305 μl L-ascorbic acid 2-phosphate (Sigma cat. A8960, 100 mg/ml stock), 6.5 ml GlutMax (ThermoFisher cat. 35050-079), 50 ng/ml bFGF (Peprotech, cat. 100-18B), and 1.5 ng/ml TGFβ-I (Peprotech, cat. 100-21C). (2) DMEM/Vc: could be used as day 0-1, day 0-2, day 0-5, etc. differentiation medium DMEM basal medium (ThermoFisher, cat. 11965-092) with 60 μg/m1L-ascorbic acid (Sigma, A8960); (3) LaSR basal medium: could be used as day 1-4, day 0-4, day 1-5, day 0-5, day 0-16, etc. differentiation medium.

Advanced DMEM/F12 (Thermo cat. 12634-028), 305 μl L-ascorbic acid 2-phosphate (Sigma cat. A8960, 100 mg/ml stock), 6.5 ml GlutMax (Thermo cat. 35050-079). Stemline II medium (Sigma, S0192): could be used as day 0-4, day 0-6, 5-16, day 6-16, day 0-16, etc. differentiation medium; StemSpan H3000 (Stemcell Technologies, 09850): could be used as day 0-4, day 0-6, 5-16, day 6-16, day 0-16, etc. differentiation medium; DMEM/Vc+15% or 20% human AB-serum: could be used as day 5-16, day 6-16, day 0-16, etc. differentiation medium; DMEM basal medium (ThermoFisher, cat. 11965-092)+60 μ/ml L-ascorbic acid (Sigma, A8960)+15% or 20% human AB-serum (Valley Biomedical, HP1022HI or Sigma, H4522).

Part B: stem cell culture and differentiation substrate: hESC-qualified Matrigel, Corning, 354277; iMatrix-511, Iwai North America Inc, N-892021 or N-892011; Nacalai USA Inc, 892021 or 892011; Synthemax II-SC substrate, Corning, 3535; Vitronectin substrate, Stemcell Technologies, 07180; Mebiol gel for 3D culture and differentiation, Cosmo, MBG-PMW20-1001.

Part C: small molecules and growth factors: Y27632 (~5 μM~): human pluripotent stem cell culture, Cayman Chem, 10005583; CHIR99021 (~6 μM~), depend on culture medium and cell lines used, could range from 1 to 20 μM; Gsk3 inhibitor; Cayman Chem, 13122; SB431542 (~10 μM~). TGFbeta inhibitor; Cayman Chem, 13031; A83-01 (~5 μM~); TGFbeta inhibitor; Cayman Chem, 9001799; Recombinant Human VEGF165 (~50 ng/mL~), Peprotech #100-20; Recombinant Human SCF (~50 ng/mL~), Peprotech #300-07; Recombinant Human Flt3-Ligand (~50 ng/mL~), Peprotech #300-19.

Statistical Analysis.

Data are presented as mean±standard error of the mean (s.e.m). Statistical significance was determined by Student's t-test (two-tail) between two groups, and three or more groups were analyzed by one-way analysis of variance (ANOVA). $P<0.05$ was considered statistically significant.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope.

REFERENCES CITED

1. Dzierzak E, Speck N A. Of lineage and legacy: The development of mammalian hematopoietic stem cells. Nat Immunol 2008.
2. Takahashi K, Tanabe K, Ohnuki M, et al. Induction of pluripotent stem cells from adult human fibroblasts by defined factors. Cell 2007; 131:861-872.
3. Takahashi K, Yamanaka S. Induction of pluripotent stem cells from mouse embryonic and adult fibroblast cultures by defined factors. Cell 2006; 126:663-676.
4. Godin I, Dieterlen-Lièvre F, Cumano A. Emergence of multipotent hemopoietic cells in the yolk sac and paraaortic splanchnopleura in mouse embryos, beginning at 8.5 days postcoitus. Proc Natl Acad Sci USA 1995.
5. Ditadi A, Sturgeon C M, Tober J, et al. Human definitive haemogenic endothelium and arterial vascular endothelium represent distinct lineages. Nat Cell Biol 2015; 17:580-591.
6. Kaufman D S. Toward clinical therapies using hematopoietic cells derived from human pluripotent stem cells. Blood 2009.
7. McKinney-Freeman S, Cahan P, Li H, et al. The transcriptional landscape of hematopoietic stem cell ontogeny. Cell Stem Cell 2012.
8. Kennedy M, Awong G, Sturgeon C M, et al. T Lymphocyte Potential Marks the Emergence of Definitive Hematopoietic Progenitors in Human Pluripotent Stem Cell Differentiation Cultures. Cell Rep 2012; 2:1722-1735.
9. Ivanovs A, Rybtsov S, Ng E S, et al. Human haematopoietic stem cell development: from the embryo to the dish. Development 2017; 144:2323-2337.
10. Ng E S, Azzola L, Bruveris F F, et al. Differentiation of human embryonic stem cells to HOXA+hemogenic vasculature that resembles the aorta-gonad-mesonephros. Nat Biotechnol 2016; 34:1168-1179.
11. Ivanovs A, Rybtsov S, Ng E S, et al. Human haematopoietic stem cell development: from the embryo to the dish. Development 2017; 144:2323-2337.
12. Rybtsov S, Ivanovs A, Zhao S, et al. Concealed expansion of immature precursors underpins acute burst of adult HSC activity in foetal liver. Development 2016; 143: 1284-1289.
13. Hatzimichael E, Tuthill M. Hematopoietic stem cell transplantation. Stem Cells Cloning 2010; 3:105-117.
14. Boisset J-C, van Cappellen W, Andrieu-Soler C, et al. In vivo imaging of haematopoietic cells emerging from the mouse aortic endothelium. Nature 2010; 464:116-120.
15. Bertrand J Y, Chi N C, Santoso B, et al. Haematopoietic stem cells derive directly from aortic endothelium during development. Nature 2010; 464:108-111.

16. Kissa K, Herbomel P. Blood stem cells emerge from aortic endothelium by a novel type of cell transition. Nature 2010; 464:112-115.
17. Lian X, Bao X, Al-Ahmad A, et al. Efficient Differentiation of Human Pluripotent Stem Cells to Endothelial Progenitors via Small-Molecule Activation of WNT Signaling. Stem Cell Reports 2014; 3:804-816.
18. Bao X, Lian X, Dunn K K, et al. Chemically-defined albumin-free differentiation of human pluripotent stem cells to endothelial progenitor cells. Stem Cell Res 2015; 15:122-129.
19. Kim I, Saunders T L, Morrison S J. Sox17 Dependence Distinguishes the Transcriptional Regulation of Fetal from Adult Hematopoietic Stem Cells. Cell 2007; 130: 470-483.
20. Clarke R L, Yzaguirre A D, Yashiro-Ohtani Y, et al. The expression of Sox17 identifies and regulates haemogenic endothelium. Nat Cell Biol 2013; 15:502-510.
21. Motazedian A, Bruveris F F, Kumar S V., et al. Multipotent RAG1+ progenitors emerge directly from haemogenic endothelium in human pluripotent stem cell-derived haematopoietic organoids. Nat Cell Biol 2020; 22:60-73.
22. Palpant N J, Pabon L, Friedman C E, et al. Generating high-purity cardiac and endothelial derivatives from patterned mesoderm using human pluripotent stem cells. Nat Protoc 2017; 12:15-31.
23. Jung M, Cordes S. Zou J, et al. GATA2 deficiency and human hematopoietic development modeled using induced pluripotent stem cells. Blood Adv 2018; 2:3553-3565.
24. Sturgeon C M, Ditadi A, Awong G, et al. Wnt signaling controls the specification of definitive and primitive hematopoiesis from human pluripotent stem cells. Nat Biotechnol 2014; 32:554-561.
25. Jung H S, Uenishi G I, Park M A, et al. SOX17 Is Essential for Integration of Arterial and HOXA Programs in Hemogenic Endothelium. Blood 2019; 134:2476-2476.
26. Nakajima-Takagi Y, Osawa M, Oshima M, et al. Role of SOX17 in hematopoietic development from human embryonic stem cells. Blood 2013; 121:447-458.
27. Wang C, Tang X, Sun X, et al. TGFβ inhibition enhances the generation of hematopoietic progenitors from human E S cell-derived hemogenic endothelial cells using a stepwise strategy. Cell Res 2012; 22:194-207.
28. Kirmizitas A, Meiklejohn S, Ciau-Uitz A, et al. Dissecting BMP signaling input into the gene regulatory networks driving specification of the blood stem cell lineage. Proc Natl Acad Sci USA 2017; 114:5814-5821.
29. Crisan M, Kartalaei P S, Vink C, et al. BMP signalling differentially regulates distinct haematopoietic stem cell types. Nat Commun 2015; 6:1-9.
30. Chanda B, Ditadi A. Iscove N N, et al. Retinoic acid signaling is essential for embryonic hematopoietic stem cell development. Cell 2013; 155:215-227.
31. Uenishi G I, Jung H S, Kumar A, et al. NOTCH signaling specifies arterial-type definitive hemogenic endothelium from human pluripotent stem cells. Nat Commun 2018; 9:1828.
32. Galat Y, Dambaeva S, Elcheva I. et al. Cytokine-free directed differentiation of human pluripotent stem cells efficiently produces hemogenic endothelium with lymphoid potential. Stem Cell Res Ther 2017; 8:67.
33. Lian X J, Hsiao C, Wilson G, et al. Robust cardiomyocyte differentiation from human pluripotent stem cells via temporal modulation of canonical Wnt signaling. Proc Natl Acad Sci USA 2012; 109:E1848-E1857.
34. North T E, De Bruijn MFTR, Stacy T, et al. Runxl expression marks long-term repopulating hematopoietic stem cells in the midgestation mouse embryo Immunity 2002; 16:661-672.
35. Notta F, Zandi S, Takayama N. et al. Distinct routes of lineage development reshape the human blood hierarchy across ontogeny. Science (80-) 2016; 351.
36. Inoue S I, Noda S, Kashima K, et al. Mitochondrial respiration defects modulate differentiation but not proliferation of hematopoietic stem and progenitor cells. FEBS Lett 2010; 584:3402-3409.
37. Siatecka M, Bicker J J. The multifunctional role of EKLF/KLF1 during erythropoiesis. Blood 2011; 118: 2044-2054.
38. McGrath K E, Frame J M, Fegan K H, et al. Distinct Sources of Hematopoietic Progenitors Emerge before HSCs and Provide Functional Blood Cells in the Mammalian Embryo. Cell Rep 2015; 11:1892-1904.
39. Oatley M, Bölükbasi ÖV, Svensson V, et al. Single-cell transcriptomics identifies CD44 as a marker and regulator of endothelial to haematopoietic transition. Nat Commun 2020; 11.
40. Fidanza A, RomanòN, Ramachandran P, et al. Single cell transcriptome analysis reveals markers of naïve and lineage-primed hematopoietic progenitors derived from human pluripotent stem cells. BioRxiv 2019:602565.
41. Zöller M. CD44, hyaluronan, the hematopoietic stem cell, and leukemia-initiating cells. Front Immunol 2015; 6:235.
42. Cao H, Heazlewood S Y, Williams B, et al. The role of CD44 in fetal and adult hematopoietic stem cell regulation. Haematologica 2016; 101:26-37.
43. Trapnell C. Cacchiarelli D, Grimsby J, et al. The dynamics and regulators of cell fate decisions are revealed by pseudotemporal ordering of single cells. Nat Biotechnol 2014; 32:381-386.
44. Motazedian A, Bruveris F F, Kumar S V., et al. Multipotent RAG1+ progenitors emerge directly from haemogenic endothelium in human pluripotent stem cell-derived haematopoietic organoids. Nat Cell Biol 2020; 22:60-73.
45. Qian P, De Kumar B, He X C, et al. Retinoid-Sensitive Epigenetic Regulation of the Hoxb Cluster Maintains Normal Hematopoiesis and Inhibits Leukemogenesis. Cell Stem Cell 2018; 22:740-754.e7.
46. Chen J Y, Miyanishi M, Wang S K, et al. Hoxb5 marks long-term haematopoietic stem cells and reveals a homogenous perivascular niche. Nature 2016; 530:223-227.
47. Gulati G S, Zukowska M, Noh J, et al. Neogenin-1 distinguishes between myeloid-biased and balanced Hoxb5+ mouse long-term hematopoietic stem cells. BioRxiv 2019:608398.
48. Bao X, Bhute V J, Han T, et al. Human pluripotent stem cell-derived epicardial progenitors can differentiate to endocardial-like endothelial cells. Bioeng Transl Med 2017.
49. Mesquitta W-T, Wandsnider M, Kang H, et al. UM171 expands distinct types of myeloid and N K progenitors from human pluripotent stem cells. Sci Rep 2019; 9:6622.
50. Heazlewood S Y, Oteiza A, Cao H, et al. Analyzing hematopoietic stem cell homing, lodgment, and engraftment to better understand the bone marrow niche. Ann N Y Acad Sci 2014; 1310:119-128.
51. Staal FJT, Spaink H P, Fibbe W E. Visualizing Human Hematopoietic Stem Cell Trafficking in Vivo Using a Zebrafish Xenograft Model. Stem Cells Dev 2016; 25:360-365.

52. Hamilton N, Sabroe I, Renshaw S A. A method for transplantation of human HSCs into zebrafish, to replace humanised murine transplantation models. F1000Research 2018; 7:594.
53. Taoudi S, Gonneau C. Moore K, et al. Extensive hematopoietic stem cell generation in the AGM region via maturation of VE-Cadherin+CD45+ pre-definitive HSCs. Cell Stem Cell 2008; 3:99-108.
54. Rybtsov S, Sobiesiak M, Taoudi S, et al. Hierarchical organization and early hematopoietic specification of the developing HSC lineage in the AGM region. J Exp Med 2011; 208:1305-1315.
55. Zhou F, Li X, Wang W, et al. Tracing haematopoietic stem cell formation at single-cell resolution. Nature 2016; 533:487-492.
56. Chang Y, Hellwarth P B, Randolph L N, et al. Fluorescent indicators for continuous and lineage-specific reporting of cell-cycle phases in human pluripotent stem cells. Biotechnol Bioeng 2020:bit.27352.
57. Randolph L N, Bao X, Oddo M, et al. Sex-dependent VEGF expression underlies variations in human pluripotent stem cell to endothelial progenitor differentiation. Sci Rep 2019; 9:16696.
58. Konermann S, Lotfy P, Brideau N J, et al. Transcriptome Engineering with RNA-Targeting Type VI-D CRISPR Effectors. Cell 2018; 173:665-676.e14.
59. Wessels H H, Mèndez-Mancilla A, Guo X, et al. Massively parallel Cas13 screens reveal principles for guide RNA design. Nat Biotechnol 2020; 38:722-727.
60. Randolph L N, Bao X, Zhou C, et al. An all-in-one, Tet-On 3G inducible PiggyBac system for human pluripotent stem cells and derivatives. Sci Rep 2017; 7:1549.
61. Fuerer C, Nusse R. Lentiviral vectors to probe and manipulate the Wnt signaling pathway. PLoS One 2010; 5.
62. Kumar A, Lee J H, Suknantha K, et al. NOTCH activation at the hematovascular mesoderm stage facilitates efficient generation of T cells with high proliferation potential from human pluripotent stem cells. J Immunol 2019; 202:770.
63. Kim D, Paggi J M, Park C, et al. Graph-based genome alignment and genotyping with HISAT2 and HISAT-genotype. Nat Biotechnol 2019; 37:907-915.
64. Ramsköld D, Wang E T, Burge C B, et al. An abundance of ubiquitously expressed genes revealed by tissue transcriptome sequence data. PLoS Comput Bio12009; 5:e1000598.
65. Oprescu S N, Yue F, Qiu J, et al. Temporal Dynamics and Heterogeneity of Cell Populations during Skeletal Muscle Regeneration. IScience 2020; 23.
66. Stuart T, Butler A, Hoffman P, et al. Comprehensive Integration of Single-Cell Data. Cell 2019; 177:1888-1902.e21.
67. Soza-Ried C, Hess I, Netuschil N, et al. Essential role of c-myb in definitive hematopoiesis is evolutionarily conserved. Proc Natl Acad Sci USA 2010; 107:17304-17308.

The invention claimed is:

1. A method for generating hematopoietic stem cells (HSCs) and progenitor cells from human pluripotent stem cells (hPSCs) comprising the steps of:

a. preparing human pluripotent stem cells (hPSCs);

b. preparing a culture medium comprising a glycogen synthase kinase-3 (GSK3) inhibitor, wherein said GSK3 inhibitor is to activate the canonical Wnt signaling pathway of said hPSCs;

c. culturing the undifferentiated hPSCs in the culture medium containing the GSK3 inhibitor to activate the canonical Wnt signaling pathway in the undifferentiated hPSCs and initiate differentiation in the undifferentiated hPSCs; and d. then downregulating the activated canonical Wnt signaling pathway or transforming growth factor beta (TGF-beta) signaling pathway for a period of time to induce and generate said hematopoietic stem cells (HSCs).

2. The method according to claim 1, further comprising addition of a stem cell factor (SCF) or a Flt3-ligand in the culture medium of step d for an improved constancy of batch to batch operation.

3. The method according to claim 1, wherein said human pluripotent cells comprises human embryonic stem cells (hESC) lines selected from the group consisting of H9, H1, and H13; and human induced pluripotent cell lines selected from the group consisting of 19-9-11, 6-9-9, and Kolf2.

4. The method according to claim 1, wherein said downregulating the activated canonical Wnt signaling pathway is effected by a Wnt inhibitor, SB431542, a beta-catenin shRNA, a beta-catenin-targeted Cas13d, or a Cas9 gRNA.

5. The method according to claim 4, wherein said Wnt inhibitor comprises Wnt-C59 and IWP2.

6. The method according to claim 5, wherein functional concentration of said Wnt inhibitor ranges from about 0.2 μM to about 20 μM.

7. The method according to claim 5, wherein said Wnt-C59 has a formula:

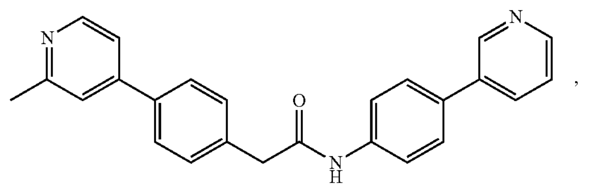 [SMILES: Cc1cc(-c2ccc(CC(=O)Nc3ccc(-c4cccnc4)cc3)cc2)ccn1]

or is a pharmaceutically acceptable salt thereof.

8. The method according to claim 5, wherein said IWP-2 has a formula:

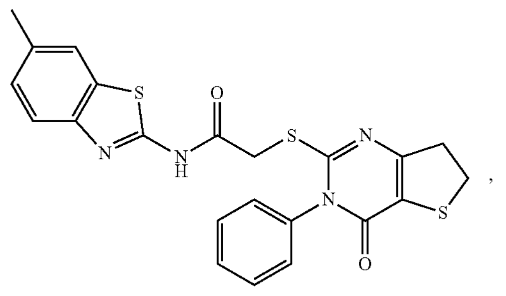 [SMILES: Cc1ccc2nc(NC(=O)CSc3nc4c(c(=O)n3-c3ccccc3)SCC4)sc2c1]

or is a pharmaceutically acceptable salt thereof.

9. The method according to claim 1, wherein said downregulating TGF-beta signaling pathway is effected by a TGF-beta inhibitor, SB431542, A83-01, a ALK5 inhibitor, polyvinyl alcohol (PVA), a TGF-beta shRNA, a TGF-beta-targeted Cas13d, or a Cas9 gRNA, wherein the downregulating is performed after differentiation of the hPSCs into hemogenic endothelium.

10. The method according to claim 9, wherein functional concentration of said SB431542 ranges from about 0.2 μM to about 20 μM.

11. The method according to claim 9, wherein said SB431542 has a formula:

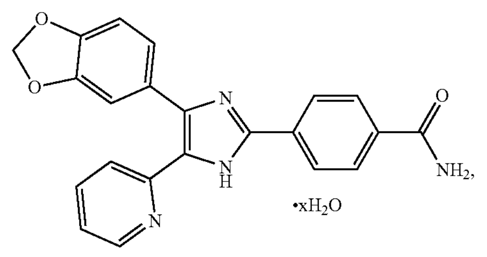 [SMILES: NC(=O)c1ccc(-c2nc(-c3ccc4c(c3)OCO4)c(-c3ccccn3)[nH]2)cc1]

or is a pharmaceutically acceptable salt thereof, wherein x is any number.

12. The method according to claim 9, wherein said A83-01 has a formula:

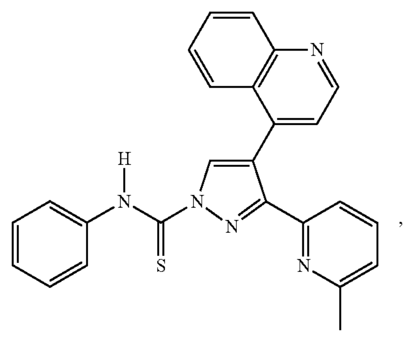 [SMILES: Cc1cccc(-c2nn(C(=S)Nc3ccccc3)cc2-c2ccnc3ccccc23)n1]

or is a pharmaceutically acceptable salt thereof, wherein x is any number.

13. The method according to claim 9, wherein the concentration of said A83-01 ranges from about 0.2 μM to about 20 μM.

14. The method according to claim 1, wherein said GSK3 inhibitor comprises CHIR99021, CHIR98014, BIO, MeBIO, LY2090314, lithium chloride, and Indirubin.

15. The method according to claim 14, wherein said CHIR99021 has a formula:

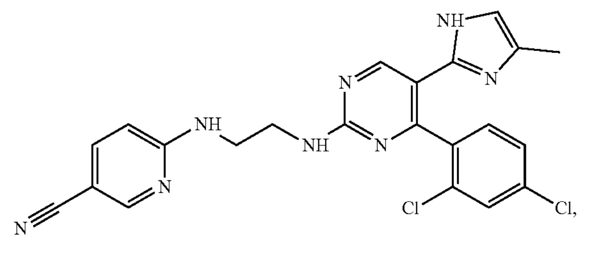 [SMILES: Cc1c[nH]c(-c2cnc(NCCNc3ccc(C#N)cn3)nc2-c2ccc(Cl)cc2Cl)n1]

or a salt thereof.

16. The method according to claim 14, wherein CHIR98014 has a formula:

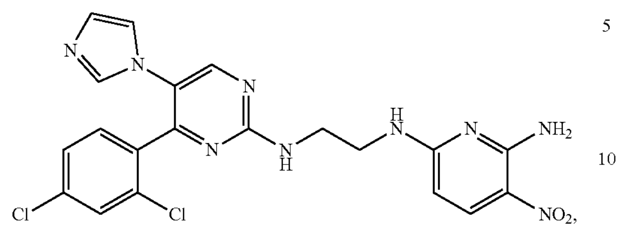

or a salt thereof.

17. The method according to claim 14, wherein the concentration of said CHIR99021 or CHIR98014 ranges from about 0.2 μM to about 20 μM.

18. The method according to claim 1, wherein said HSCs are aorta-gonad-mesonephros-like $SOX17^{+}CD34^{+}$ HSCs or progenitor cells, and general $CD34^{+}CD45^{+}/CD43^{+}$ hematopoietic progenitor cells.

19. The method according to claim 1, comprising as step b:

preparing a culture medium comprising a vascular endothelial growth factor (VEGF) and a glycogen synthase kinase-3 (GSK3) inhibitor, wherein said GSK3 inhibitor is to activate the canonical Wnt signaling pathway of said hPSCs.

* * * * *